(12) United States Patent
Nicolau et al.

(10) Patent No.: US 7,745,423 B2
(45) Date of Patent: Jun. 29, 2010

(54) CALCIUM/SODIUM SALT OF INOSITOL TRIPYROPHOSPHATE AS AN ALLOSTERIC EFFECTOR OF HEMOGLOBIN

(75) Inventors: Yves Claude Nicolau, Newton, MA (US); Jean-Marie Lehn, Strasbourg (FR); Konstantina C. Fylaktakidou, Thessaloniki (GR); Ruth Greferath, Kehl (DE)

(73) Assignees: NormOxys, Inc, Brighton, MA (US); Universite de Strasbourg, Strasbourg Cedex (FR)

(*) Notice: Subject to any disclaimer, the term of this patent is extended or adjusted under 35 U.S.C. 154(b) by 0 days.

(21) Appl. No.: 12/130,005

(22) Filed: May 30, 2008

(65) Prior Publication Data

US 2009/0029951 A1    Jan. 29, 2009

Related U.S. Application Data

(63) Continuation-in-part of application No. 11/497,566, filed on Aug. 1, 2006, which is a continuation-in-part of application No. 11/396,338, filed on Mar. 31, 2006, which is a continuation-in-part of application No. 11/175,979, filed on Jul. 6, 2005, and a continuation-in-part of application No. 11/384,012, filed on Mar. 17, 2006.

(60) Provisional application No. 60/585,804, filed on Jul. 6, 2004, provisional application No. 60/663,491, filed on Mar. 18, 2005.

(51) Int. Cl.
    *A61K 31/66* (2006.01)
(52) U.S. Cl. .................................... 514/102
(58) Field of Classification Search ............... 514/102
    See application file for complete search history.

(56) References Cited

U.S. PATENT DOCUMENTS

| 4,192,869 | A | 3/1980 | Nicolau et al. |
| 4,321,259 | A | 3/1982 | Nicolau et al. |
| 4,404,150 | A | 9/1983 | Tsunekawa et al. |
| 4,473,496 | A | 9/1984 | Scannon |
| 4,478,824 | A | 10/1984 | Franco et al. |
| 4,650,786 | A | 3/1987 | Wong |
| 4,652,449 | A | 3/1987 | Ropars et al. |
| 4,699,926 | A | 10/1987 | Abraham et al. |
| 4,710,488 | A | 12/1987 | Wong |
| 4,731,381 | A | 3/1988 | Abraham et al. |
| 4,731,473 | A | 3/1988 | Abraham et al. |
| 4,735,936 | A | 4/1988 | Sirén |
| 4,751,244 | A | 6/1988 | Abraham et al. |
| 4,752,586 | A | 6/1988 | Ropars et al. |
| 4,777,134 | A | 10/1988 | Siren |
| 4,794,014 | A | 12/1988 | Siren |
| 4,797,390 | A | 1/1989 | Siren |
| 4,826,675 | A | 5/1989 | Gaffar et al. |
| 4,847,082 | A | 7/1989 | Sabin |
| 4,851,560 | A | 7/1989 | Siren |
| 4,873,355 | A | 10/1989 | Hobbs et al. |
| 4,874,690 | A | 10/1989 | Goodrich, Jr. et al. |
| 4,887,995 | A | 12/1989 | Abraham et al. |
| 4,924,023 | A | 5/1990 | Hobbs et al. |
| 4,931,276 | A | 6/1990 | Franco et al. |
| 4,952,396 | A | 8/1990 | Sabin et al. |
| 4,952,717 | A | 8/1990 | Ozaki et al. |
| 5,003,098 | A | 3/1991 | Siren et al. |
| 5,015,634 | A | 5/1991 | Siren |
| 5,019,566 | A | 5/1991 | Siren |
| 5,023,248 | A | 6/1991 | Siren |
| 5,043,261 | A | 8/1991 | Goodrich et al. |
| 5,051,411 | A | 9/1991 | Siren |
| 5,057,507 | A | 10/1991 | Siren |
| 5,082,833 | A | 1/1992 | Shamsuddin |
| 5,091,549 | A | 2/1992 | Ozaki et al. |
| 5,135,923 | A | 8/1992 | Siren |
| 5,151,539 | A | 9/1992 | Bright et al. |
| 5,210,263 | A | 5/1993 | Kozikowski et al. |
| 5,252,707 | A | 10/1993 | Ozaki et al. |
| 5,260,287 | A | 11/1993 | Barreto et al. |
| 5,260,472 | A | 11/1993 | Chen |

(Continued)

FOREIGN PATENT DOCUMENTS

EP    0 392 697 A2    10/1990

(Continued)

OTHER PUBLICATIONS

Kobayashi et al, "Oxygenation of Hypoxic Region in Solid Tumor by Administration of Human Serum Albumin Incorporating Synthetic Hemes". J Biomed Mater Res; 64A:2003; 48-51.*

(Continued)

*Primary Examiner*—Ardin Marschel
*Assistant Examiner*—Leslie A Royds
(74) *Attorney, Agent, or Firm*—Ropes & Gray LLP

(57) ABSTRACT

The present invention relates to mixed calcium/sodium salt of inositol tripyrophosphate, methods of preparing and methods of use. The mixed calcium/sodium salt may be a monocalcium tetrasodium salt of inositol tripyrophosphate. Methods of use include administering the above salts in an effective amount to treat diseases caused by hypoxia or other conditions associated with inadequate function of the lungs or circulatory system, such as various types of cancer and Alzheimer's disease.

2 Claims, 7 Drawing Sheets

U.S. PATENT DOCUMENTS

| | | | |
|---|---|---|---|
| 5,264,605 | A | 11/1993 | Ozaki et al. |
| 5,274,161 | A | 12/1993 | Siren et al. |
| 5,292,913 | A | 3/1994 | Ozaki et al. |
| 5,295,944 | A | 3/1994 | Teicher et al. |
| 5,296,466 | A | 3/1994 | Kilbourn et al. |
| 5,330,979 | A | 7/1994 | Siren et al. |
| 5,344,393 | A | 9/1994 | Roth et al. |
| 5,407,924 | A | 4/1995 | Siren |
| 5,428,007 | A | 6/1995 | Fischer et al. |
| 5,451,205 | A | 9/1995 | Roth et al. |
| 5,545,632 | A | 8/1996 | Siren |
| 5,612,207 | A | 3/1997 | Nicolau et al. |
| 5,626,884 | A | 5/1997 | Lockett |
| 5,720,921 | A | 2/1998 | Meserol |
| 5,827,837 | A | 10/1998 | Bevilacqua et al. |
| 5,846,957 | A | 12/1998 | Siren |
| 5,866,548 | A | 2/1999 | Tsien et al. |
| 5,866,557 | A | 2/1999 | Persson et al. |
| 5,880,099 | A | 3/1999 | Traynor-Kaplan et al. |
| 5,977,078 | A | 11/1999 | Traynor-Kaplan et al. |
| 6,004,938 | A | 12/1999 | Frick et al. |
| 6,074,605 | A | 6/2000 | Meserol et al. |
| 6,096,916 | A | 8/2000 | Aneja |
| 6,187,335 | B1 | 2/2001 | Brey et al. |
| 6,610,702 | B2 | 8/2003 | Lehn et al. |
| 7,084,115 | B2 | 8/2006 | Nicolau et al. |
| 7,084,126 | B1 | 8/2006 | Frey, II et al. |
| 2002/0028786 | A1 | 3/2002 | Frey, II et al. |
| 2002/0142995 | A1 | 10/2002 | Nicolau et al. |
| 2002/0173494 | A1 | 11/2002 | Lehn et al. |
| 2003/0017150 | A1 | 1/2003 | Torphy |
| 2003/0147937 | A1 | 8/2003 | Schwarz |
| 2004/0014642 | A1 | 1/2004 | Nicolau et al. |
| 2004/0072801 | A1 | 4/2004 | Nicolau et al. |
| 2004/0147487 | A1 | 7/2004 | Traylor-Kaplan et al. |
| 2005/0020542 | A1 | 1/2005 | Traynor-Kaplan et al. |
| 2005/0227946 | A1 | 10/2005 | Siren |
| 2005/0250743 | A1 | 11/2005 | Lehn et al. |
| 2005/0272642 | A1 | 12/2005 | Frey, II et al. |
| 2006/0009413 | A1 | 1/2006 | Frey, II et al. |
| 2006/0014716 | A1 | 1/2006 | Frey, II et al. |
| 2006/0030542 | A1 | 2/2006 | Frey, II et al. |
| 2006/0106000 | A1 | 5/2006 | Nicolau et al. |
| 2006/0116358 | A1 | 6/2006 | Nicolau et al. |
| 2006/0241086 | A1 | 10/2006 | Nicolau et al. |
| 2006/0258626 | A1 | 11/2006 | Nicolau et al. |
| 2007/0066574 | A1 | 3/2007 | Grases Freixedas |
| 2007/0129336 | A1 | 6/2007 | Traynor-Kaplan |
| 2007/0135389 | A1 | 6/2007 | Nicolau et al. |
| 2007/0207986 | A1 | 9/2007 | Nicolau et al. |

FOREIGN PATENT DOCUMENTS

| | | |
|---|---|---|
| EP | 0 508 488 B1 | 10/1992 |
| JP | 52-107239 | 9/1977 |
| JP | 1-175989 | 7/1989 |
| WO | WO 87/05598 A1 | 9/1987 |
| WO | WO 92/20369 | 11/1992 |
| WO | WO 94/21117 A1 | 9/1994 |
| WO | WO 95/03068 | 2/1995 |
| WO | WO 95/05830 A1 | 3/1995 |
| WO | WO 96/32136 | 10/1996 |
| WO | WO 01/013933 | 3/2001 |
| WO | WO 01/15738 | 3/2001 |
| WO | WO 01/24830 A2 | 4/2001 |
| WO | WO 01/82932 A2 | 11/2001 |
| WO | WO 02/09723 A2 | 2/2002 |
| WO | WO 02/10177 A1 | 2/2002 |
| WO | WO 03/092700 A1 | 11/2003 |
| WO | WO 2006/102060 A1 | 9/2006 |

OTHER PUBLICATIONS

Fylaktakidou et al. "Inositol Tripyrophosphate: A New Membrane Permeant Allosteric Effector of Haemoglobin". Bioorganic and Medicinal Chemistry Letters; 15(2005):1605-1608.*

Title: EntreMed Annual Report, Publ: *EDGAR Online*, pp. 1-40, Date: Mar. 3, 2000.

Author: Adachi et al., Title: Nucleation-Controlled Aggregation of Deoxyhemoglobins—Effect of Organic Phosphates on the Kinetics of Aggregation of DeoxyhemoglobinS in Concentrated Phosphate Buffer, Publ: *Biochimica et Biophysica Acta*, vol./Iss: 624, pp. 372-377, Date: Aug. 21, 1980.

Author: Amorino et al., Title: Enhancement of Tumor Oxygenation and Radiation Response by the Allosteric Effector of Hemoglobin, RSR13, Publ: *Radiation Research*, vol./Iss: 156, pp. 1, Date: Oct. 12, 2000.

Author: Arnone, A., Title: X-ray Diffraction Study of Binding of 2,3-Diphosphoglycerate to Human Deoxyhaemoglobin, Publ: *Nature*, vol./Iss: 237 (5350), pp. 146-149, Date: May 12, 1972.

Author: Benesch et al., Title: The Effect of Organic Phosphates from the Human Erythrocyte on the Allosteric Properties of Hemoglobin, Publ: *Biochemical and Biophysical Research Communications*, vol./Iss: 26 (2), pp. 162-167, Date: Jan. 23, 1967.

Author: Benesch et al., Title: Intracellular Organic Phosphates as Regulators of Oxygen Release by Haemoglobin, Publ: *Nature*, vol./Iss: 221, pp. 618-622, Date: Feb. 15, 1969.

Author: Cosgrove, D.J., Title: The Phosphorylation of *epi*-Inositol and *muco*-Inositol with Polyphosphoric Acid, Publ: *Carbohydrate Research*, vol./Iss: 40, pp. 380-384, Date: Jan. 1, 1975.

Author: Desai et al., Title: The Preparation, Resolution, and Phosphorylation of Some Benzyl Ethers of *myo*-Inositol: Intermediates for the Synthesis of *myo*-Inositol Phosphates of the Phosphotidylinositol Cycle, Publ: *Carbohydrate Research*, vol./Iss: 225, pp. 209-228, Date: Mar. 1, 1992.

Author: Dinkel et al., Title: Membrane-Permeant 3-OH-Phosphorylated Phosphoinositide Derivatives, Publ: *Angewandte Chemie International Edition*, vol./Iss: 40 (16), pp. 3004-3008, Date: Aug. 17, 2001.

Author: Fisher, J., Title: Erythropoietin: Physiology and Pharmacology Update, Publ: *Society for Experimental Biology and Medicines*, vol./Iss: 228(1), pp. 1-14, Date: Jan. 1, 2003.

Author: Fylaktakidou et al., Title: Inositol Triphosphate: A New Membrane Permeant Allosteric Effector of Haemoglobin, Publ: *Bioorganic & Medicinal Chemistry Letters*, vol./Iss: 15, pp. 1605-1608, Date:Jan. 1, 2005.

Author: Gersonde et al., Title: Modification of the Oxygen Affinity of Intracellular Haemoglobin by Incorporation of Polyphosphates into Intact Red Blood Cells and Enhanced $O_2$ Release in theCapillary System, Publ: *Bibliotheca Haematologica*, vol./Iss: 46, pp. 81-92, Date: Sep. 1, 1980.

Author: Gutman et al., Title: Failure of Thalidomide to Inhibit Tumor Growth and Angiogenesis in Vivo, Publ: *Anticancer Research*, vol./Iss: 16, pp. 3673-3678, Date: Jan. 1, 1996.

Author: Hockel et al., Title: Tumor Hypoxia: Definitions and Current Clinical, Biologic, and Molecular Aspects, Publ: *Journal of the National Cancer Institute*, vol./Iss: 93(4), pp. 266-276, Date: Feb. 21, 2001.

Author: Huang et al., Title: Identification and Purification of Diphosphoinositol Pentakisphosphate Kinase, Which Synthesizes the Inositol Pyrophosphate Bis(diphospho)inositol Tetrakisphosphate, Publ: *Biochemistry*, vol./Iss: 37, pp. 14998-15004, Date: Jan. 1, 1998.

Author: Ishii et al., Title: Decreased Medial Temporal Oxygen Metabolism in Alzheimer's Disease Shown by PET, Publ: *The Journal of Nuclear Medicine*, vol./Iss: 37(7), pp. 1159-1165, Date: Jul. 1, 1996.

Author: Johnson, L.F., Title: Structure of "Phytic Acids", Publ: *Canadian Journal of Chemistry*, vol./Iss: 47, pp. 63-73, Date: Jan. 1, 1969.

Author: Kilgore et al., Title: RSR13, a Synthetic Allosteric Modifier of Hemoglobin, Improves Myocardial Recovery Following Hypothermic Cardiopulmonary Bypass, Publ: *Circulation*, vol./Iss: 100:II-351, pp. 1-15, Date: Jan. 1, 1999.

Author: Lee et al., Title: Synthesis of Mono and Unsymmetrical Bis Ortho Esters of scyllo-Inositol, Publ: *Journal of Organic Chemistry*, vol./Iss: 50, pp. 4402-4404, Date: Jan. 1, 1985.

Author: Lu et al., Title: Molecular Interactions ofEndogenous D-*myo*-Inositol Phosphates with the Intracellular D-*myo*-Inositol 1,4,5-Trisphosphate Recognition Site, Publ: *Biochemistry*, vol./Iss: 33, pp. 11586-11597, Date: Jan. 1, 1994.

Author: Luo et al., Title: Inositol Pyrophosphates are Required for DNA Hyperrecombination in Protein Kinase C1 Mutant Yeast, Publ: *Biochemistry*, vol./Iss: 41, pp. 2509-2515, Date: Jan. 1, 2002.

Author: Menniti et al., Title: Turnover of Inositol PolyphosphatePyrophosphates in Pancreatoma Cells, Publ: *The Journal of Biological Chemistry*, vol./Iss: 68 (6), pp. 3850-3856, Date: Jan. 1, 1993.

Author: Montchamp et al., Title: Butane 2,3-Bisacetal Protection of Vicinal Diequatorial Diols, Publ: *Journal of Orgnaic Chemistry*, vol./Iss: 61, pp. 3897-3899, Date: Jan. 1, 1996.

Author: Nicolau et al., Title: Incorporation of Allosteric Effectors of Hemoglobin in Red Blood Cells. Physiologic Effects, Publ: *Bibliotheca Haematologica*, vol./Iss: 51, pp. 92-107, Date: Jan. 1, 1985.

Author: Noble et al., Title: Total Synthesis of Myo-Inositol-1-Phosphate-4,5-Pyrophosphate, aNovel Second Messenger Analogue, via Myo-Inositol-1-Phosphate-4,5-Bisphosphorthioate, Publ: *Bioorganic & Medicinal Chemistry Letters*, vol./Iss: 2 (5), pp. 471-476, Date: Jan. 1, 1992.

Author: Oshiro et al., Title: Regulation of the *DPP1*-encoded Diacyglycerol Pyrophosphate (DGPP) Phosphatase by Inositol and Growth Phase, Publ: *The Journal of Biological Chemistry*, vol./Iss: 275 (52), pp. 40887-40896, Date: Dec. 29, 2000.

Author: Pagel et al., Title: RSR13, a Synthetic Modifier of Hemoglobin-Oxygen Affinity, Enhances the Recovery of Stunned Myocardium in Anesthetized Dogs (Applicants do not have complete copy), Publ: *Pharmacology*, vol./Iss: 285 (1), pp. 1-8, Date: Apr. 1, 1998, (Applicants do not have complete copy).

Author: Poillon et al., Title: Deoxygenated Sickle Hemoglobin Modulation of its Solubility by 2,3-diphosphoglycerate and other Allosteric Polyanions(Applicants do not have complete copy), Publ: *The Journal of Biological Chemistry*, vol./Iss: 260 (26), pp. 13897-13900, Date: Nov. 15, 1985.

Author: Ruckpaul et al., Title: Interaction of Hemoglobin with Ions AllostericEffects of the Binding of Anions, Publ: *Biochemica et Biophysica Acta*, vol./Iss: 236, pp. 211-221, Date: Jan. 1, 1971.

Author: Saiardi et al., Title: Mammalian Inositol Polyphosphate Multikinase Synthesizes Inositol 1,4,5-Trisphosphate and an Inositol Pyrophosphate, Publ: *Proceedings of the National Academy of Sciences of the USA*, vol./Iss: 98 (5), pp. 2306-2311, Date: Feb. 27, 2001.

Author: Shannon et al., Title: Tumour Hypoxia, Chemotherapeutic Resistance and Hypoxia-Related Therapies, Publ: *Cancer Treatment Reviews*, vol./Iss: 29, pp. 297-307, Date: Jan. 1, 2003.

Author: Stadelmaier et al., Title: Synthesis of Phosphotidylinositol Mannosides (PIMs), Publ: *Carbohydrate Research*, vol./Iss: 338, pp. 2557-2569, Date: Nov. 1, 2003.

Author: Teicher et al., Title: Allosteric Effectors of Hemoglobin as Modulators of Chemotherapy and Radiation Therapy in Vitro and in Vivo (Applicants do not have complete copy), Publ: *Cancer Chemotherapy Pharmacology*, vol./Iss: 42 (1), pp. 24-30, Date: Jan. 1, 1998.

Author: Teisseire et al., Title: Physiological Effects of High-$P_{50}$ Erythrocyte Transfusion on Piglets, Publ: *Journal of Applied Physiology*, vol./Iss: 58 (6), pp. 1810-1817, Date: Jun. 1, 1985.

Author: Thomas et al., Title: Current Role of Thalidomide in Cancer Treatment, Publ: *Current Opinions in Oncology*, vol./Iss: 12, pp. 564-573, Date: Jan. 1, 2000.

Author: Vacca et al., Title: The Total Synthesis of myo-Inositol Polyphosphates, Publ: *Tetrahedron*, vol./Iss: 45 (17), pp. 5679-5702, Date: Jan. 1, 1989.

Author: Vacca et al., Title: Chapter 5: Synthesis of myo-Inositol Polyphosphates, Publ: *ACS Symposium Series*, pp. 67-85, Date: Aug. 26, 1990.

Author: Vincent et al., Title: Transport of the Highly Charged Myo-inositol Hexakisphosphate Molecule Across the Red Blood Cell Membrane: A Phase Transfer and Biological Study, Publ: *Bioorganic & Medicinal Chemistry Letters*, vol./Iss: 10 (9), pp. 2825-2834, Date: Sep. 1, 2002.

Author: Vucenik et al., Title: Anti-Angiogenic Activity of Inositol Hexaphosphate ($IP_6$) (Applicants do not have complete copy), Publ: *Carcinogenesis*, vol./Iss: 25 (11), pp. 2115-2123, Date: Jan. 1, 2004.

Author: Ye et al., Title: Inhibition of Clathrin Assembly by High Affinity Binding of Specific Inositol Polyphosphates to the Synapse-specific Clathrin Assembly Protein AP-3, Publ: *The Journal of Biological Chemistry*, vol./Iss: 270 (4), pp. 1564-1568, Date: Jan. 1, 1995.

Title: U.S. Appl. No. 11/497,566—Office Action, Publ: USPTO, pp. 1-8, Date: Apr. 7, 2009.

Title: U.S. Appl. No. 11/497,566—Office Action, Date: Aug. 3, 2009.

Title: U.S. Appl. No. 11/328,313—Office Action, Publ: USPTO, pp. 1-8, Date: Dec. 10, 2008.

Title: U.S. Appl. No. 11/600,685—Office Action, Publ: USPTO, pp. 1-7, Date: Nov. 28, 2008.

Title: U.S. Appl. No. 11/384,012—Final Office Action, Publ: USPTO, pp. 1-5, Date: Nov. 17, 2008.

Title: U.S. Appl. No. 11/384,012—Office Action, Publ: USPTO, pp. 1-6, Date: Apr. 29, 2008.

Title: U.S. Appl. No. 11/175,979—Office Action, Publ: USPTO, pp. 1-10, Date: Jul. 22, 2008.

Title: U.S. Appl. No. 11/384,012—Office Action, Publ: USPTO, pp. 1-7, Date: Jul. 8, 2009.

Title: U.S. Appl. No. 11/396,338—Final Office Action, Publ: USPTO, pp.1-7, Date: Aug. 20, 2008.

PCT Search Report—PCT/2006/09682. pp. 1-2, Jun. 23, 2006.

Vascular Morphology, *Advances in Chemical Engineering*, vol. 19, p. 147, Jan. 1, 1994.

*EPO Search Report*—EPO Application 0372488 0, pp. 1-4 , Sep. 29, 2009.

*EPO Search Report* cited in EPO Application 07754611.7. pp. 1-13, Oct. 14, 2009.

Folkman, J. Models of Anti-Cancer Therapy: Angiogenesis Inhibitors: A New Class of Drugs. *Cancer Biology & Therapy.* vol. 2. 4 Suppl 1, pp. S127-S133, Jan. 1, 2003.

Newbert, Daniel W. Transcription Factors and Cancer: An Overview. *Toxicology.* vol. 181-182, pp. 131-141, Jan. 1, 2002.

Singh et al. In Vivo Suppression of Hormone-Refractory Prostate Cancer Growth by Inositol Hexaphosphate: Induction of Insulin-Like Growth Factor Binding Protein-3 and Inhibition of Vascular Endothelial Growth Factor. *Clinical Cancer Research.* vol. 10, pp. 244-250, Jan. 1, 2004.

Smith, S.K. Angiogenesis, Vascular Endothelial Growth Factor and the Endometrium. *Human Reproduction Update.* vol. 4 No. 5, pp. 509-519, Jan. 1998.

Soria, J. et al. Molecular Targeting' Targeting Angiogenesis in Solid Tumors. *Annals of Oncology.* vol. 15 (suppl 4), pp. iv223-iv227, Jan. 1, 2004.

Sutton, Darryl C—*USPTO*, Office Action cited in U.S. Appl. No. 11/175,979. pp. 1-11, Oct. 26, 2009.

* cited by examiner

CALCIUM/SODIUM SALT OF INOSITOL TRIPYROPHOSPHATE AS AN ALLOSTERIC EFFECTOR OF HEMOGLOBIN

CROSS-REFERENCE TO RELATED APPLICATIONS

This application is a continuation-in-part of U.S. patent application Ser. No. 11/497,566 filed Aug. 1, 2006, which is a continuation-in-part of U.S. application Ser. No. 11/396,338 filed Mar. 31, 2006 which is a continuation-in-part of U.S. patent application Ser. Nos. 11/175,979 filed Jul. 6, 2005, and 11/384,012 filed Mar. 17, 2006, all of which are incorporated herein by reference in their entirety. U.S. patent application Ser. No. 11/175,979 claims the benefit of priority to U.S. Provisional Patent Application No. 60/585,804 filed Jul. 6, 2004, which is incorporated herein by reference in its entirety. U.S. patent application Ser. No. 11/384,012 claims the benefit of priority to U.S. Provisional Patent Application No. 60/663,491 filed Mar. 18, 2005, which is incorporated herein by reference in its entirety.

FIELD OF THE INVENTION

The present invention is directed to compositions and methods for using the mixed calcium/sodium salt of inositol-tripyrophosphate (ITPP-Ca/Na) to enhance oxygen delivery by red blood cells. ITPP-Ca/Na is an allosteric effector of hemoglobin which has the ability to cross the plasma membrane of red blood cells and lower the oxygen affinity of the hemoglobin of red blood cells. The present invention is further directed to the use of ITPP-Ca/Na to inhibit angiogenesis and enhance radiation sensitivity of hypoxic tumors. The present invention is further directed to the use of ITPP-Ca/Na to enhance the partial pressure of oxygen ($PO_2$) in hypoxic tumors.

BACKGROUND OF THE INVENTION

In the vascular system of an adult human being, blood has a volume of about 5 to 6 liters. Approximately one half of this volume is occupied by cells, including red blood cells (erythrocytes), white blood cells (leukocytes), and blood platelets. Red blood cells comprise the majority of the cellular components of blood. Plasma, the liquid portion of blood, is approximately 90 percent water and 10 percent various solutes. These solutes include plasma proteins, organic metabolites and waste products, and inorganic compounds.

The major function of red blood cells is to transport oxygen from the lungs to the tissues of the body, and transport carbon dioxide from the tissues to the lungs for removal. Very little oxygen is transported by the blood plasma because oxygen is only sparingly soluble in aqueous solutions. Most of the oxygen carried by the blood is transported by the hemoglobin of the erythrocytes. Erythrocytes in mammals do not contain nuclei, mitochondria or any other intracellular organelles, and they do not use oxygen in their own metabolism. Red blood cells contain about 35 percent by weight hemoglobin, which is responsible for binding and transporting oxygen.

Hemoglobin is a protein having a molecular weight of approximately 64,500 daltons. It contains four polypeptide chains and four heme prosthetic groups in which iron atoms are bound in the ferrous state. Normal globin, the protein portion of the hemoglobin molecule, consists of two alpha chains and two beta chains. Each of the four chains has a characteristic tertiary structure in which the chain is folded. The four polypeptide chains fit together in an approximately tetrahedral arrangement, to constitute the characteristic quaternary structure of hemoglobin. There is one heme group bound to each polypeptide chain which can reversibly bind one molecule of molecular oxygen. When hemoglobin combines with oxygen, oxyhemoglobin is formed. When oxygen is released, the oxyhemoglobin is reduced to deoxyhemoglobin.

Delivery of oxygen to tissues, including tumors, depends upon a number of factors including, but not limited to, the volume of blood flow, the number of red blood cells, the concentration of hemoglobin in the red blood cells, the oxygen affinity of the hemoglobin and, in certain species, on the molar ratio of intraerythrocytic hemoglobins with high and low oxygen affinity. The oxygen affinity of hemoglobin depends on four factors as well, namely: (1) the partial pressure of oxygen; (2) the pH; (3) the concentration of 2,3-diphosphoglycerate (DPG) in the hemoglobin; and (4) the concentration of carbon dioxide. In the lungs, at an oxygen partial pressure of 100 mm Hg, approximately 98% of circulating hemoglobin is saturated with oxygen. This represents the total oxygen transport capacity of the blood. When fully oxygenated, 100 ml of whole mammalian blood can carry about 21 ml of gaseous oxygen.

The effect of the partial pressure of oxygen and the pH on the ability of hemoglobin to bind oxygen is best illustrated by examination of the oxygen saturation curve of hemoglobin. An oxygen saturation curve plots the percentage of total oxygen-binding sites of a hemoglobin molecule that are occupied by oxygen molecules when solutions of the hemoglobin molecule are in equilibrium with different partial pressures of oxygen in the gas phase.

The oxygen saturation curve for hemoglobin is sigmoid. Thus, binding the first molecule of oxygen increases the affinity of the remaining hemoglobin for binding additional oxygen molecules. As the partial pressure of oxygen is increased, a plateau is approached at which each of the hemoglobin molecules is saturated and contains the upper limit of four molecules of oxygen.

The reversible binding of oxygen by hemoglobin is accompanied by the release of protons, according to the equation:

$$HHb^+ + O_2 \rightleftharpoons HbO_2 + H^+$$

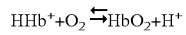

Thus, an increase in the pH will pull the equilibrium to the right and cause hemoglobin to bind more oxygen at a given partial pressure. A decrease in the pH will decrease the amount of oxygen bound.

In the lungs, the partial pressure of oxygen in the air spaces is approximately 90 to 100 mm Hg and the pH is also high relative to normal blood pH (up to 7.6). Therefore, hemoglobin will tend to become almost maximally saturated with oxygen in the lungs. At that pressure and pH, hemoglobin is approximately 98 percent saturated with oxygen. On the other hand, in the capillaries in the interior of the peripheral tissues, the partial pressure of oxygen is only about 25 to 40 mm Hg and the pH is also nearly neutral (about 7.2 to 7.3). Because muscle cells use oxygen at a high rate, thereby lowering the local concentration of oxygen, the release of some of the bound oxygen to the tissue is favored. As the blood passes through the capillaries in the muscles, oxygen will be released from the nearly saturated hemoglobin in the red blood cells into the blood plasma and then into the muscle cells. Hemoglobin will release about a fourth of its bound oxygen as it passes through the muscle capillaries, so that when it leaves the muscle, it will be only about 75 percent saturated. In general, the hemoglobin in the venous blood leaving the tissue cycles between about 65 and 97 percent saturation with oxygen in its repeated circuits between the lungs and the peripheral tissues. Thus, oxygen partial pressure and pH function together to effect the release of oxygen by hemoglobin.

A third important factor in regulating the degree of oxygenation of hemoglobin is the allosteric effector 2,3-diphosphoglycerate (DPG). DPG is the normal physiological effector of hemoglobin in mammalian erythrocytes. DPG regulates the oxygen-binding affinity of hemoglobin in the red blood cells in relationship to the oxygen partial pressure in the lungs. The higher the concentration of DPG in the cell, the lower the affinity of hemoglobin for oxygen.

When the delivery of oxygen to the tissues is chronically reduced, the concentration of DPG in the erythrocytes is higher than in normal individuals. For example, at high altitudes the partial pressure of oxygen is significantly less. Correspondingly, the partial pressure of oxygen in the tissues is less. Within a few hours after a normal human subject moves to a higher altitude, the DPG level in the red blood cells increases, causing more DPG to be bound and the oxygen affinity of the hemoglobin to decrease. Increases in the DPG level of red cells also occur in patients suffering from hypoxia. This adjustment allows the hemoglobin to release its bound oxygen more readily to the tissues to compensate for the decreased oxygenation of hemoglobin in the lungs. The reverse change occurs when people are acclimated to high altitudes and descend to lower altitudes.

As normally isolated from blood, hemoglobin contains a considerable amount of DPG. When hemoglobin is "stripped" of its DPG, it shows a much higher affinity for oxygen. When DPG is increased, the oxygen binding affinity of hemoglobin decreases. A physiologic allosteric effector such as DPG is therefore essential for the normal release of oxygen from hemoglobin in the tissues.

While DPG is the normal physiologic effector of hemoglobin in mammalian red blood cells, phosphorylated inositols are found to play the same role in the erythrocytes of some birds and reptiles. Although inositol hexaphosphate (IHP) is unable to pass through the mammalian erythrocyte membrane, it is capable of combining with hemoglobin of mammalian red blood cells at the binding site of DPG to modify the allosteric conformation of hemoglobin, the effect of which is to reduce the affinity of hemoglobin for oxygen. For example, DPG can be replaced by IHP, which is far more potent than DPG in reducing the oxygen affinity of hemoglobin. IHP has a 1000-fold higher affinity to hemoglobin than DPG (R. E. Benesch et al., Biochemistry, Vol. 16, pages 2594-2597 (1977)) and increases the $P_{50}$ of hemoglobin up to values of 96.4 mm, Hg at pH 7.4, and 37 degrees C. (J. Biol. Chem., Vol. 250, pages 7093-7098 (1975)).

The oxygen release capacity of mammalian red blood cells can be enhanced by introducing certain allosteric effectors of hemoglobin into erythrocytes, thereby decreasing the affinity of hemoglobin for oxygen and improving the oxygen economy of the blood. This phenomenon suggests various medical applications for treating individuals who are experiencing lowered oxygenation of their tissues due to the inadequate function of their lungs or circulatory system.

Because of the potential medical benefits to be achieved from the use of these modified erythrocytes, various techniques have been developed in the prior art to enable the encapsulation of allosteric effectors of hemoglobin in erythrocytes. Accordingly, numerous devices have been designed to assist or simplify the encapsulation procedure. The encapsulation methods known in the art include osmotic pulse (swelling) and reconstitution of cells, controlled lysis and resealing, incorporation of liposomes, and electroporation. Current methods of electroporation make the procedure commercially impractical on a scale suitable for commercial use.

The following references describe the incorporation of polyphosphates into red blood cells by the interaction of liposomes loaded with IHP: Gersonde, et al., "Modification of the Oxygen Affinity of Intracellular Hemoglobin by Incorporation of Polyphosphates into Intact Red Blood Cells and Enhanced $O_2$ Release in the Capillary System", Biblthca. Haemat., No. 46, pp. 81-92 (1980); Gersonde, et al., "Enhancement of the $O_2$ Release Capacity and of the Bohr-Effect of Human Red Blood Cells after Incorporation of Inositol Hexaphosphate by Fusion with Effector-Containing Lipid Vesicles", Origins of Cooperative Binding of Hemoglobin (1982); and Weiner, "Right Shifting of Hb-$O_2$ Dissociation in Viable Red Cells by Liposomal Technique," Biology of the Cell, Vol. 47, (1983).

Additionally, U.S. Pat. Nos. 4,192,869, 4,321,259, and 4,473,563 to Nicolau et al. describe a method whereby fluid-charged lipid vesicles are fused with erythrocyte membranes, depositing their contents into the red blood cells. In this manner, it is possible to transport allosteric effectors, such as IHP into erythrocytes, where due to its much higher binding constant IHP replaces DPG at its binding site in hemoglobin.

In accordance with the liposome technique, IHP is dissolved in a phosphate buffer until the solution is saturated and a mixture of lipid vesicles is suspended in the solution. The suspension is then subjected to ultrasonic treatment or an injection process, and then centrifuged. The upper suspension contains small lipid vesicles containing IHP, which are then collected. Erythrocytes are added to the collected suspension and incubated, during which time the lipid vesicles containing IHP fuse with the cell membranes of the erythrocytes, thereby depositing their contents into the interior of the erythrocyte. The modified erythrocytes are then washed and added to plasma to complete the product.

The drawbacks associated with the liposomal technique include poor reproducibility of the IHP concentrations incorporated in the red blood cells and significant hemolysis of the red blood cells following treatment. Additionally, commercialization is not practical because the procedure is tedious and complicated.

In an attempt to solve the drawbacks associated with the liposomal technique, a method of lysing and the resealing red blood cells was developed. This method is described in the following publication: Nicolau, et al., "Incorporation of Allosteric Effectors of Hemoglobin in Red Blood Cells. Physiologic Effects," Biblthca. Haemat., No. 51, pp. 92-107, (1985). Related U.S. Pat. Nos. 4,752,586 and 4,652,449 to Ropars et al. also describe a procedure of encapsulating substances having biological activity in human or animal erythrocytes by controlled lysis and resealing of the erythrocytes, which avoids the red blood cell-liposome interactions.

The technique is best characterized as a continuous flow dialysis system, which functions in a manner similar to the osmotic pulse technique. Specifically, the primary compartment of at least one dialysis element is continuously supplied with an aqueous suspension of erythrocytes, while the secondary compartment of the dialysis element contains an aqueous solution which is hypotonic with respect to the erythrocyte suspension. The hypotonic solution causes the erythrocytes to lyse. The erythrocyte lysate is then contacted with the biologically active substance to be incorporated into the erythrocyte. To reseal the membranes of the erythrocytes, the osmotic and/or oncotic pressure of the erythrocyte lysate is increased and the suspension of resealed erythrocytes is recovered.

In related U.S. Pat. Nos. 4,874,690 and 5,043,261 to Goodrich et al., a related technique involving lyophilization and reconstitution of red blood cells is disclosed. As part of the process of reconstituting the red blood cells, the addition of various polyanions, including IHP, is described. Treatment of the red blood cells according to the process disclosed results in a cell with unaffected activity. Presumably, the IHP is incorporated into the cell during the reconstitution process, thereby maintaining the activity of the hemoglobin.

In U.S. Pat. Nos. 4,478,824 and 4,931,276 to Franco et al., a second related method and apparatus is described for introducing effectively non-ionic agents, including IHP, into mammalian red blood cells by effectively lysing and resealing the cells. The procedure is described as the "osmotic pulse technique." In practicing the osmotic pulse technique, a supply of packed red blood cells is suspended and incubated in a solution containing a compound which readily diffuses into and out of the cells, the concentration of the compound being sufficient to cause diffusion thereof into the cells so that the contents of the cells become hypertonic. Next, a trans-membrane ionic gradient is created by diluting the solution containing the hypertonic cells with an essentially isotonic aqueous medium in the presence of at least one desired agent to be introduced, thereby causing diffusion of water into the cells with a consequent swelling and an increase in permeability of the outer membranes of the cells. This "osmotic pulse" causes the diffusion of water into the cells and a resultant swelling of the cells which increase the permeability of the outer cell membrane to the desired agent. The increase in permeability of the membrane is maintained for a period of time sufficient only to permit transport of at least one agent into the cells and diffusion of the compound out of the cells.

Polyanions which may be used in practicing the osmotic pulse technique include pyrophosphate, tripolyphosphate, phosphorylated inositols, 2,3-diphosphoglycerate (DPG), adenosine triphosphate, heparin, and polycarboxylic acids which are water-soluble, and non-disruptive to the lipid outer bilayer membranes of red blood cells.

The osmotic pulse technique has several shortcomings including low yield of encapsulation, incomplete resealing, loss of cell content and a corresponding decrease in the life span of the cells. The technique is tedious, complicated and unsuited to automation. For these reasons, the osmotic pulse technique has had little commercial success.

Another method for encapsulating various biologically-active substances in erythrocytes is electroporation. Electroporation has been used for encapsulation of foreign molecules in different cell types, including IHP in red blood cells, as described in Mouneimne, et al., "Stable rightward shifts of the oxyhemoglobin dissociation curve induced by encapsulation of inositol hexaphosphate in red blood cells using electroporation," FEBS, Vol. 275, No. 1, 2, pp. 117-120 (1990). Also, see U.S. Pat. No. 5,612,207.

Angiogenesis is the generation of new blood vessels into a tissue or organ and is related to oxygen tension in the tissues. Under normal physiological conditions, humans and animals undergo angiogenesis only in very specific, restricted situations. For example, angiogenesis is normally observed in wound healing, fetal and embryonal development, and formation of the corpus luteum, endometrium and placenta.

Angiogenesis is controlled through a highly regulated system of angiogenic stimulators and inhibitors. The control of angiogenesis is altered in certain disease states and, in many cases, pathological damage associated with the diseases is related to uncontrolled angiogenesis. Both controlled and uncontrolled angiogenesis are thought to proceed in a similar manner. Endothelial cells and pericytes, surrounded by a basement membrane, form capillary blood vessels. Angiogenesis begins with the erosion of the basement membrane by enzymes released by endothelial cells and leukocytes. Endothelial cells, lining the lumen of blood vessels, then protrude through the basement membrane. Angiogenic stimulants induce the endothelial cells to migrate through the eroded basement membrane. The migrating cells form a "sprout" off the parent blood vessel where the endothelial cells undergo mitosis and proliferate. The endothelial sprouts merge with each other to form capillary loops, creating a new blood vessel.

Persistent, unregulated angiogenesis occurs in many disease states, tumor metastases, and abnormal growth by endothelial cells. The diverse pathological disease states in which unregulated angiogenesis is present have been grouped together as angiogenic-dependent or angiogenic-associated diseases.

The hypothesis that tumor growth is angiogenesis-dependent was first proposed in 1971. (Folkman, *New Eng. J. Med.*, 285:1182-86 (1971)). In its simplest terms, this hypothesis states: "Once tumor 'take' has occurred, every increase in tumor cell population must be preceded by an increase in new capillaries converging on the tumor." Tumor 'take' is currently understood to indicate a prevascular phase of tumor growth in which a population of tumor cells occupying a few cubic millimeters volume, and not exceeding a few million cells, can survive on existing host microvessels. Expansion of tumor volume beyond this phase requires the induction of new capillary blood vessels. For example, pulmonary micrometastases in the early prevascular phase in mice would be undetectable except by high power microscopy on histological sections.

Angiogenesis has been associated with a number of different types of cancer, including solid tumors and blood-borne tumors. Solid tumors with which angiogenesis has been associated include, but are not limited to, rhabdomyosarcomas, retinoblastoma, Ewing's sarcoma, neuroblastoma, and osteosarcoma. Angiogenesis is also associated with blood-borne tumors, such as leukemias, any of various acute or chronic neoplastic diseases of the bone marrow in which unrestrained proliferation of white blood cells occurs, usually accompanied by anemia, impaired blood clotting, and enlargement of the lymph nodes, liver and spleen. It is believed that angiogenesis plays a role in the abnormalities in the bone marrow that give rise to leukemia tumors and multiple myeloma diseases.

One of the most frequent angiogenic diseases of childhood is the hemangioma. A hemangioma is a tumor composed of newly formed blood vessels. In most cases, the tumors are benign and regress without intervention. In more severe cases, the tumors progress to large cavernous and infiltrative forms and create clinical complications. Systemic forms of hemangiomas, hemangiomatoses, have a high mortality rate. Therapy-resistant hemangiomas exist that cannot be treated with therapeutics currently in use.

Another angiogenesis associated disease is rheumatoid arthritis. The blood vessels in the synovial lining of the joints undergo angiogenesis. In addition to forming new vascular networks, the endothelial cells release factors and reactive oxygen species that lead to pannus growth and cartilage destruction. Angiogenesis may also play a role in osteoarthritis. The activation of the chondrocytes by angiogenic-related factors contributes to the destruction of the joint. At a later stage, the angiogenic factors promote new bone growth. Therapeutic intervention that prevents the cartilage destruction could halt the progress of the disease and provide relief for persons suffering with arthritis.

Chronic inflammation may also involve pathological angiogenesis. Such diseases as ulcerative colitis and Crohn's disease show histological changes with the ingrowth of new blood vessels into inflamed tissues. Bartonelosis, a bacterial infection found in South America, can result in a chronic stage that is characterized by proliferation of vascular endothelial cells. Another pathological role associated with angiogenesis is found in atherosclerosis. The plaques formed within the lumen of blood vessels have been shown to have angiogenic stimulatory activity.

As mentioned above, several lines of evidence indicate that angiogenesis is essential for the growth and persistence of solid tumors and their metastases. Once angiogenesis is stimulated, tumors upregulate the production of a variety of angiogenic factors, including fibroblast growth factors (aFGF and bFGF) and vascular endothelial growth factor/vascular permeability factor (VEGF/VPF) [2,3].

The role of VEGF in the regulation of angiogenesis has been the object of intense investigation [5-10]. Whereas VEGF represents a critical, rate-limiting step in physiological angiogenesis, it appears to be also important in pathological angiogenesis, such as that associated with tumor growth [11]. VEGF is also known as vascular permeability factor, based on its ability to induce vascular leakage [13]. Several solid tumors produce ample amounts of VEGF, which stimulates proliferation and migration of endothelial cells, thereby inducing neovascularization [12,13]. VEGF expression has been shown to significantly affect the prognosis of different kinds of human cancer. Oxygen tension in the tumor has a key role in regulating the expression of VEGF gene. VEGF mRNA expression is induced by exposure to low oxygen tension under a variety of pathophysiological circumstances [13]. Growing tumors are characterized by hypoxia, which induces expression of VEGF and may also be a predictive factor for the occurrence of metastatic disease.

What is needed, therefore, is a substantially non-toxic composition and method that can regulate oxygen tension in the tissue, especially a tumor. In addition, what is needed is a simple and easily administered, preferably orally, composition that is capable of causing significant right shifts of the $P_{50}$ value for red blood cells.

SUMMARY OF THE INVENTION

The present invention provides a composition comprising the mixed calcium/sodium salt of inositol-tripyrophosphate (ITPP-Ca/Na) that is effective in treating diseases characterized by abnormal angiogenesis. The compositions and methods of the present invention have a distinct advantage over the prior art in that the compositions and methods of the present invention are substantially non-toxic and demonstrate improved solubility when compared to compositions in the prior art.

The present invention also comprises a pharmaceutical composition comprising the calcium/sodium salt of ITPP and a pharmaceutically acceptable adjuvant, diluent, carrier, or excipient thereof. In this pharmaceutical composition, the inositol tripyrophosphate is optimally myo-inositol 1,6:2,3:4,5 tripyrophosphate. In an alternate embodiment the composition may comprise the monocalcium tetrasodium salt of myo-inositol 1,6:2,3:4,5 tripyrophosphate.

The present invention also provides for substantially non-toxic methods of using the above compositions of ITPP-Ca/Na for increasing the regulated delivery of oxygen to tissues including tumors. For example, the regulation of vascular endothelial growth factor (VEGF) in a human or animal can be effected using ITPP-Ca/Na which has entered the red blood cell, thus lowering the affinity for oxygen of circulating erythrocytes. In an embodiment of the present invention, ITPP-Ca/Na can affect VEGF mRNA expression, protein concentration, and tumor cell proliferation. Also, a method of regulating VEGF expression, both in vitro and in vivo, using ITPP-Ca/Na is contemplated and therefore within the scope of the present invention.

The present invention further comprises methods for using the above compositions of ITPP-Ca/Na in pure hemoglobin and in red blood cells to deliver oxygen to solid tumors, to inhibit angiogenesis and to enhance radiation sensitivity of hypoxic tumors. The present invention is further directed to the use of ITPP-Ca/Na to enhance $PO_2$ in hypoxic tumors. ITPP-Ca/Na is an allosteric effector of hemoglobin and is capable of reducing hemoglobin's affinity for oxygen, which enhances the release of oxygen by hemoglobin. Upon cellular demand, ITPP-Ca/Na can inhibit VEGF expression in tumor cells and, thus, angiogenesis.

A disease characterized by undesirable angiogenesis or undesirable angiogenesis, as defined herein includes, but is not limited to, excessive or abnormal stimulation of endothelial cells (e.g. atherosclerosis), blood borne tumors, solid tumors and tumor metastasis, benign tumors, for example, hemangiomas, acoustic neuromas, neurofibromas, trachomas, and pyogenic granulomas, vascular malfunctions, abnormal wound healing, inflammatory and immune disorders, Bechet's disease, gout, or gouty arthritis, diabetic retinopathy and other ocular angiogenic diseases such as retinopathy of prematurity (retrolental fibroplasic), macular degeneration, corneal graft rejection, neovascular glaucoma and Osler Weber syndrome (Osler-Weber-Rendu disease). Cancers that can be treated by the present invention include, but is not limited to, breast cancer, prostrate cancer, renal cell cancer, brain cancer, ovarian cancer, colon cancer, bladder cancer, pancreatic cancer, stomach cancer, esophageal cancer, cutaneous melanoma, liver cancer, lung cancer, testicular cancer, kidney cancer, bladder cancer, cervical cancer, lymphoma, parathyroid cancer, penile cancer, rectal cancer, small intestine cancer, thyroid cancer, uterine cancer, Hodgkin's lymphoma, lip and oral cancer, skin cancer, leukemia or multiple myeloma.

An object of the invention is to provide a substantially non-toxic composition and method for treating cancer and other angiogenic disease states and conditions using ITPP-Ca/Na in an effective dose.

Another object of the invention is to provide a composition and method for enhancing oxygen delivery to hypoxic tumors using ITPP-Ca/Na in an effective dose.

Yet another object of the invention is to provide a composition and method for inhibiting angiogenesis using ITPP-Ca/Na in an effective dose.

A further object of the invention is to provide a composition and method for enhancing radiation sensitivity of hypoxic tumors using ITPP-Ca/Na in an effective dose.

It is yet another object of the invention to provide a composition and method of treating hypoxic tumors and diseases using ITPP-Ca/Na in an effective dose.

Another object of the invention is to provide a composition and method using ITPP-Ca/Na in an effective dose that can regulate oxygen tension in the tissue, especially a tumor.

A further object of the invention is to provide a simple and easily administered, preferably oral, composition that is capable of causing significant right shifts of the $P_{50}$ value for red blood cells using ITPP-Ca/Na in an effective dose.

These and other objects, features and advantages of the present invention will become apparent after a review of the following detailed description of the disclosed embodiments.

DETAILED DESCRIPTION OF THE INVENTION

Figure 1:
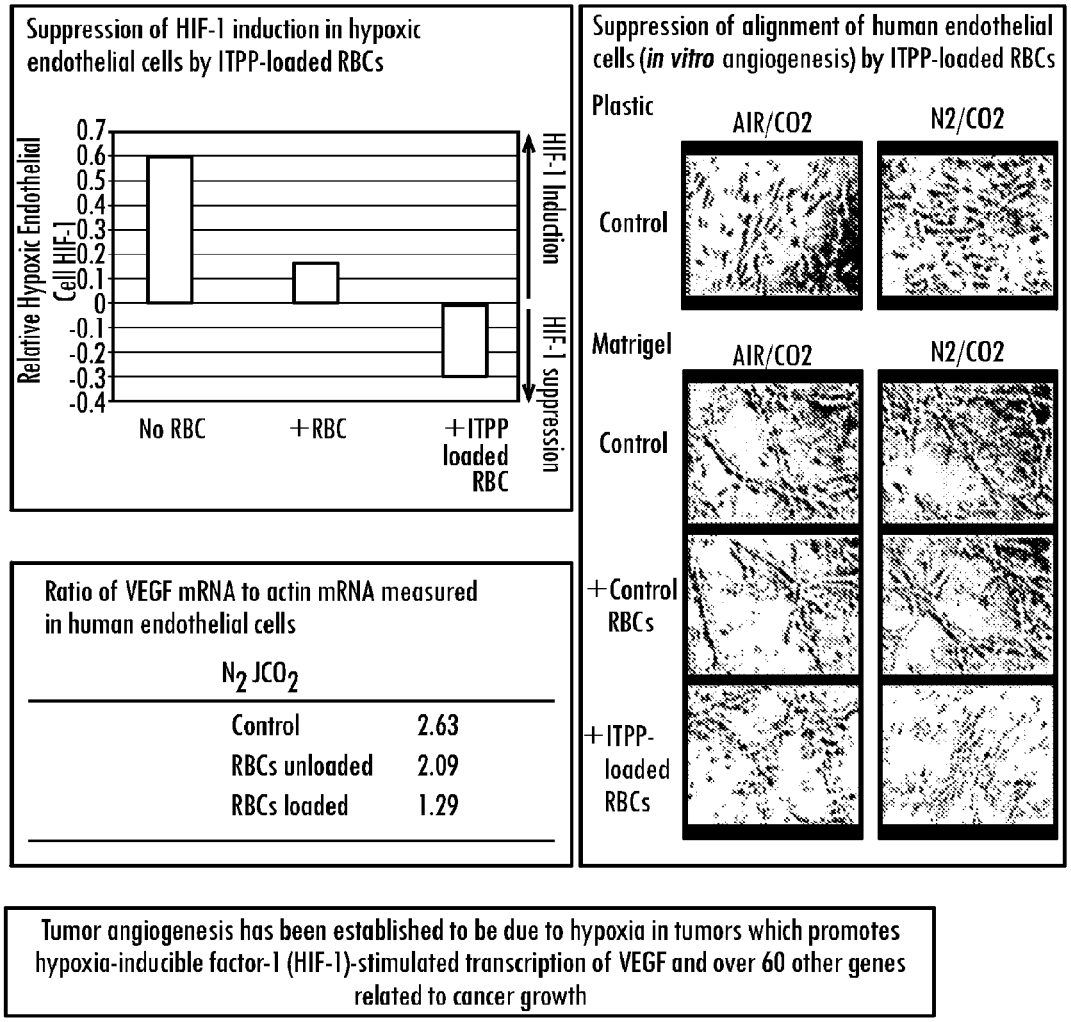
FIG. 1 shows ITPP-Ca/Na loaded red blood cell suppression of HIF-1 induction, VEGF and angiogenesis of hypoxic endothelial cells in vitro.

Compositions that are useful in accordance with the present invention include the mixed calcium/sodium salt of inositol-tripyrophosphate (ITPP-Ca/Na). ITPP exhibits antiangiogenic and anti-tumor properties, and is useful in controlling angiogenesis-, or proliferation-related events, conditions or substances. As used herein, the control of an angiogenic-, or proliferation-related event, condition, or substance refers to any qualitative or quantitative change in any type of factor, condition, activity, indicator, chemical or combination of chemicals, mRNA, receptor, marker, mediator, protein, transcriptional activity or the like, that may be or is believed to be related to angiogenesis or proliferation, and that results from administering the composition of the present invention. Those skilled in the art will appreciate that the invention extends to other compositions or compounds in the claims below, having the described characteristics. These characteristics can be determined for each test compound using the assays detailed below and elsewhere in the literature.

Other such assays include counting of cells in tissue culture plates or assessment of cell number through metabolic assays or incorporation into DNA of labeled (radiochemically, for example $^3$H-thymidine, or fluorescently labeled) or immunoreactive (BrdU) nucleotides. In addition, antiangiogenic activity may be evaluated through endothelial cell migration, endothelial cell tubule formation, or vessel outgrowth in ex-vivo models, such as rat aortic rings.

When administered orally, ITPP exhibits anti-tumor and anti-proliferative activity with little or no toxicity. ITPP was tested for its ability to induce a decrease of the $O_2$-affinity of hemoglobin measured as a shift of the $P_{50}$ value ($P_{50}$ at 50% saturation of hemoglobin). With murine hemoglobin and whole blood, $P_{50}$ shifts to higher $PO_2$ of up to 250% with hemoglobin and up to 40% with whole blood were observed.

The results obtained with ITPP in mice and pigs strongly suggest the possibility of its development as a therapeutic, due to its ability to enhance, in a regulated manner, oxygen delivery by red blood cells in the cases of blood flow impairment.

It has been found that pigs injected intravenously with ITPP-Na at a rate of 1 g/kg weight had beneficial properties associated with the introduction of ITPP-Na into their systems (as described in U.S. Provisional Patent Application 60/585,804, which is herein incorporated by reference in its entirety); however, the introduction of ITPP-Na also resulted in a number of adverse side effects. These side effects included flushing, an increase in the heart rate, and a decrease in the $Ca^{2+}$ plasma concentration. Therefore a less toxic form of ITPP that maintains a good solubility profile is needed.

ITPP, when administered orally, intravenously, or intraperitoneally, inhibits angiogenesis in growing tumors by enhancing $PO_2$ in the forming tumors. This invention further provides for methods of regulation of vascular endothelial growth factor (VEGF) in a human or animal, by administering to the human or animal an effective amount of ITPP. More particularly, this invention provides for dose-dependent effects of ITPP on VEGF mRNA and protein expressions in the LLC cell line. VEGF gene expression in tumor bearing C57BL/6 mice was assayed and the effects of ITPP-induced down regulation of VEGF have been determined and correlated with modulation of cell proliferation. This invention resulted in the development of methods to control VEGF mRNA expression, protein concentration, and tumor cell proliferation. The results of these studies indicate a strong correlation between dose-dependent ITPP-induced down regulation of VEGF and cellular proliferation and suggests that ITPP can reduce VEGF mediated tumor angiogenesis, as well as the rate of tumor cell proliferation. Thus, down-regulation of VEGF by ITPP decreases tumor cell proliferation.

The shifting of the $P_{50}$ value to higher $O_2$-partial pressures inhibits the expression of the hypoxia gene encoding VEGF in the tumors. Expression of the hypoxia gene encoding VEGF is necessary for angiogenesis to be stimulated in tumors. If this does not occur, angiogenesis is seriously inhibited and new vessels are not formed in tumors.

The results obtained concerning VEGF expression suggests that oxygen partial pressure in tumors is elevated upon administration of ITPP, as this elevation is the cause of inhibition of expression of this hypoxia gene. This observation raises a very important question, namely, whether this enhancement of $PO_2$ may act as a powerful radiosensitizer of cancer cells. Oxygen is a very potent radiosensitizer and, if indeed $PO_2$ in the tumors is enhanced by ITPP, this may have major consequences in enhancing the efficacy of radiation therapy of cancer.

ITPP is a potential significant adjuvant in the therapy of solid tumors as inhibitor of angiogenesis on one hand, and as a radiosensitizer on the other.

It is known that medial temporal oxygen metabolism is markedly affected in patients with mild-to-moderate Alzheimer's disease. This measure substantiated the functional impairment of the medial temporal region in Alzheimer's disease. It also known that mean oxygen metabolism in the medial temporal, as well as in the parietal and lateral temporal cortices is significantly lower in the patients that are shown to have Alzheimer's disease than in control groups without Alzheimer's disease (see Ishii et al., *J. Nucl Med.* 37(7):1159-65, July 1996, which is herein incorporated by reference in its entirety). Thus, one potential means of treating patients shown to have Alzheimer's disease is to increase oxygen across the blood brain barrier. One method of doing so would be to use an allosteric effector of hemoglobin such as treatment with ITPP, such as with the calcium/sodium salt of ITPP.

The use of ITPP, such as with the calcium/sodium salt of ITPP, may also help in the treatment of a variety of vascular diseases associated with various forms of dementia. Because the brain relies on a network of vessels to bring it oxygen-bearing blood, if the oxygen supply to the brain fails, brain cells are likely to die and this can cause symptoms of vascular dementia. These symptoms can occur either suddenly, following a stroke, or over time through a series of small strokes. Thus, one potential means of treating patients with vascular diseases associated with various forms of dementia is to increase the oxygen available to affected areas such as across the blood brain barrier. One method of doing so would be to use an allosteric effector of hemoglobin such as treatment with ITPP, such as with the calcium/sodium salt of ITPP.

Moreover, treatment of an individual with an allosteric effector of hemoglobin such as the calcium/sodium salt of ITPP may have beneficial effects for both stroke victims and osteoporosis. Although stroke and the bone-thinning disease osteoporosis are usually thought of as two distinct health problems, it has been found that there may be a connection between them. Patients who survive strokes are significantly more likely to suffer from osteoporosis, a disease that puts them at high risk for bone fractures. Often, the fractures in stroke patients occur on the side of the body that has been paralyzed from the stroke.

It is known that a stroke occurs when the supply of blood and oxygen to the brain ceases or is greatly reduced. If a portion of the brain loses its supply of nutrient-rich blood and oxygen, the bodily functions controlled by that part of the brain (vision, speech, walking, etc.) are impaired. Annually, more than 500,000 people in the United States suffer strokes and 150,000 of those people die as a result thereof. One means of increasing oxygen flow to the brain is by use of an allosteric effector of hemoglobin such as treatment with the calcium/sodium salt of ITPP. Accordingly, a potential method of treating individuals who might potentially suffer stroke or osteoporosis is by treatment of an individual with, for example, the calcium/sodium salt of ITPP.

Also contemplated by the present invention are implants or other devices comprised of the compounds or drugs of ITPP, or prodrugs thereof, where the drug or prodrug is formulated in a biodegradable or non-biodegradable polymer for sustained release. Non-biodegradable polymers release the drug in a controlled fashion through physical or mechanical processes without the polymer itself being degraded. Biodegradable polymers are designed to gradually be hydrolyzed or solubilized by natural processes in the body, allowing gradual release of the admixed drug or prodrug. The drug or prodrug can be chemically linked to the polymer or can be incorporated into the polymer by admixture. Both biodegradable and non-biodegradable polymers and the process by which drugs are incorporated into the polymers for controlled release are well known to those skilled in the art. Examples of such polymers can be found in many references, such as Brem et al., *J. Neurosurg* 74: pp. 441-446 (1991), which is herein incorporated by reference in its entirety. These implants or devices can be implanted in the vicinity where delivery is desired, for example, at the site of a tumor.

In addition to the compounds of the present invention, the pharmaceutical composition of this invention may also contain, or be co-administered (simultaneously or sequentially) with, one or more pharmacological agents of value in treating one or more disease conditions referred to hereinabove.

A person skilled in the art will be able by reference to standard texts, such as Remington's Pharmaceutical Sciences 17$^{th}$ edition, to determine how the formulations are to be made and how these may be administered.

In a further aspect of the present invention there is provided use of compounds of ITPP, such as ITPP-Ca/Na or prodrugs thereof, according to the present invention for the preparation of a medicament for the prophylaxis or treatment of conditions associated with angiogenesis or accelerated cell division or inflammation.

In a further aspect of the present invention there is provided a pharmaceutical composition comprising compounds of ITPP, such as ITPP-Ca/Na or prodrugs thereof, according to the present invention, together with a pharmaceutically acceptable carrier, diluent, adjuvant or excipient.

The pharmaceutical composition may be used for the prophylaxis or treatment of conditions associated with angiogenesis or accelerated cell division or inflammation, for treatment of Alzheimer's disease, treatment of stroke and/or osteoporosis.

In a still further aspect of the present invention there is provided a method of prophylaxis or treatment of a condition associated with angiogenesis or accelerated or increased amounts of cell division, hypertrophic growth, or inflammation, said method including administering to a patient in need of such prophylaxis or treatment an effective amount of compounds of ITPP, such as ITPP-Ca/Na or prodrugs thereof, according to the present invention, as described herein. It should be understood that prophylaxis or treatment of said condition includes amelioration of said condition.

By "an effective amount" as referred to in this specification, it is meant a therapeutically or prophylactically effective amount. Such amounts can be readily determined by an appropriately skilled person, taking into account the condition to be treated, the route of administration and other relevant factors. Such a person will readily be able to determine a suitable dose, mode and frequency of administration. "Individual" as referred to in this application refers to any animal that may be in need of treatment for a given condition. "Individual" includes humans, other primates, household pets, livestock, rodents, other mammals, and any other animal(s) that may typically be treated by a veterinarian.

The compositions described above can be provided as physiologically acceptable formulations using known techniques, and these formulations can be administered by standard routes. In general, the combinations may be administered by the topical, oral, rectal, intraperitoneal or parenteral (e.g., intravenous, subcutaneous or intramuscular) route. In addition, the combinations may be incorporated into polymers allowing for sustained release, the polymers being implanted in the vicinity of where delivery is desired, for example, at the site of a tumor, or into an a cavity or blood vessel that will lead to easy delivery to the place to be treated. The dosage of the composition will depend on the condition being treated, the particular derivative used, and other clinical factors such as weight and condition of the patient and the route of administration of the compound. However, for oral administration, a recommended dosage is in the range of 0.1 to 5.0 g/kg/day. A dosage for oral administration is in the range of 0.5 to 2.0 g/kg/day or alternatively, about 0.5 to about 1.5 g/kg/day. In an alternate embodiment, a dosage for oral administration is in the range of about 0.80 to 1.0 g/kg/day or alternatively, about between 0.9 to 1.1 g/kg/day.

The formulations in accordance with the present invention can be administered in the form of tablet, a capsule, a lozenge, a cachet, a solution, a suspension, an emulsion, a powder, an aerosol, a suppository, a spray, a pastille, an ointment, a cream, a paste, a foam, a gel, a tampon, a pessary, a granule, a bolus, a mouthwash, or a transdermal patch.

The formulations include those suitable for oral, rectal, nasal, inhalation, topical (including dermal, transdermal, buccal and sublingual), vaginal, parenteral (including subcutaneous, intramuscular, intravenous, intraperitoneal, intradermal, intraocular, intratracheal, and epidural) or inhalation administration. The formulations may conveniently be presented in unit dosage form and may be prepared by conventional pharmaceutical techniques. Such techniques include the step of bringing into association the active ingredient and a pharmaceutical carrier(s) or excipient(s). In general, the formulations are prepared by uniformly and intimately bringing into association the active ingredient with liquid carriers or finely divided solid carriers or both, and then, if necessary, shaping the product.

Formulations contemplated as part of the present invention include nanoparticles formulations made by methods disclosed in U.S. patent application Ser. No. 10/392,403 (Publication No. 2004/0033267) which is hereby incorporated by reference in its entirety. By forming nanoparticles, the compositions disclosed herein are shown to have increased bioavailability. Preferably, the particles of the compounds of the present invention have an effective average particle size of less than about 2 microns, less than about 1900 nm, less than about 1800 nm, less than about 1700 nm, less than about 1600 nm, less than about 1500 nm, less than about 1400 nm, less than about 1300 nm, less than about 1200 nm, less than about 1100 nm, less than about 1000 nm, less than about 900 nm, less than about 800 nm, less than about 700 nm, less than about 600 nm, less than about 500 nm, less than about 400 nm, less than about 300 nm, less than about 250 nm, less than about 200 nm, less than about 150 nm, less than about 100 nm, less than about 75 nm, or less than about 50 nm, as measured by light-scattering methods, microscopy, or other appropriate methods well known to those of ordinary skill in the art.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil emulsion, etc.

A tablet may be made by compression or molding, optionally with one or more accessory ingredients. Compressed tablets may be prepared by compressing, in a suitable machine, the active ingredient in a free-flowing form such as a powder or granules, optionally mixed with a binder, lubricant, inert diluent, preservative, surface-active or dispersing agent. Molded tablets may be made by molding, in a suitable machine, a mixture of the powdered compound moistened with an inert liquid diluent. The tablets may optionally be coated or scored and may be formulated so as to provide a slow or controlled release of the active ingredient therein.

Formulations suitable for topical administration in the mouth include lozenges comprising the ingredients in a flavored basis, usually sucrose and acacia or tragacanth; pastilles comprising the active ingredient in an inert basis such as gelatin and glycerin, or sucrose and acacia; and mouthwashes comprising the ingredient to be administered in a suitable liquid carrier.

Formulations suitable for topical administration to the skin may be presented as ointments, creams, gels and pastes comprising the ingredient to be administered in a pharmaceutically acceptable carrier. A preferred topical delivery system is a transdermal patch containing the ingredient to be administered.

Formulations for rectal administration may be presented as a suppository with a suitable base comprising, for example, cocoa butter and/or a salicylate.

Formulations suitable for nasal administration, wherein the carrier is a solid, include a coarse powder having a particle size, for example, in the range of 20 to 500 microns which is administered in the manner in which snuff is taken; i.e., by rapid inhalation through the nasal passage from a container of the powder held close up to the nose. Suitable formulations, wherein the carrier is a liquid, for administration, as for example, a nasal spray or as nasal drops, include aqueous or oily solutions of the active ingredient.

Formulations suitable for vaginal administration may be presented as pessaries, tampons, creams, gels, pastes, foams or spray formulations containing, in addition to the active ingredient, ingredients such as carriers as are known in the art to be appropriate.

Formulation suitable for inhalation may be presented as mists, dusts, powders or spray formulations containing, in addition to the active ingredient, ingredients such as carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in freeze-dried (lyophilized) conditions requiring only the addition of a sterile liquid carrier, for example, water for injections, immediately prior to use. Extemporaneous injection solutions and suspensions may be prepared from sterile powders, granules and tablets of the kinds previously described.

Preferred unit dosage formulations are those containing a daily dose or unit, daily sub-dose, as herein above recited, or an appropriate fraction thereof, of the administered ingredient.

It should be understood that in addition to the ingredients, particularly those mentioned above, the formulations of the present invention may include other agents conventional in the art having regard to the type of formulation in question, for example, those suitable for oral administration may include flavoring agents or other agents to make the formulation more palatable and more easily swallowed.

EXPERIMENTAL

For the in vitro experiments, ITPP was dissolved in deionized water, pH was adjusted at pH 7 and, for incubation with whole blood, the osmolarity of the ITPP solutions was adjusted with glucose to 270-297 mOsM. Mixtures of hemoglobin and ITPP were measured with a HEMOX analyzer (PD Marketing, London) immediately after mixing. Red blood cells were incubated with ITPP for 1 hour at 37° C. Following incubation, the cells were washed 3 times with Bis-Tris-buffer (pH=7.0) and then used for $P_{50}$ measurement.

In experiments conducted in vivo in which ITPP was administered orally, a significant shift of the $P_{50}$ value of circulating RBCs was observed. ITPP was dissolved in drinking water at a 20 g/L-concentration (0.27 mM, pH ~7.0.) and offered for drinking ad libitum.

The following examples illustrate but do not limit the invention. Thus, the examples are presented with the understanding that modifications may be made and still be within the spirit and scope of the invention.

Example 1

Effectiveness of the Mixed Calcium Sodium Salt of myo-Inositol Tripyrophosphate

When myo-inositol tripyrophosphate-sodium salt (ITPP-Na) is mixed with $CaCl_2$, a mixture of ITPP-Na (myo-inositol tripyrophosphate-sodium salt) and ITPP-Ca (myo-inositol tripyrophosphate-calcium salt) is obtained. This mixture, when added to free hemoglobin or to whole blood induces a $P_{50}$ shift of 170% and 25%, respectively as shown in Tables 2 and 3 below. Please see the results in Tables 2 and 3 for compound 15. The compounds in Tables 2 and 3 are as follows: 4 is the pyridinium salt of ITPP, 5 is the sodium salt of ITPP (i.e., ITPP-Na), 7 is the N,N-dimethylcyclohexyl ammonium salt of ITPP, 11 is the cycloheptyl ammonium salt of ITPP, 12 is the cyclooctyl ammonium salt of ITPP, 13 is the piperazinium salt of ITPP, 14 is the tripiperazinium salt of ITPP, and 15 is the calcium salt of ITPP (i.e., ITPP-Ca).

In Tables 2 and 3, the effectiveness of all of the salts of ITPP regarding their ability to act as allosteric effectors of hemoglobin can be seen. The sodium salt and the calcium salt of ITPP appear to be the best allosteric effectors for both free hemoglobin (Table 2) and in whole blood (Table 3). However, pigs injected intravenously with ITPP-Na at a rate of 1 g/kg weight resulted in a number of adverse side effects. The intravenous injection of pigs with ITPP-Na resulted in flushing, an increase in the heart rate, and a decrease in the $Ca^{2+}$ plasma concentration from 2.38 mmol/L to 1.76 mmol/L.

Administration of the mixture of the sodium and calcium salt of ITPP, at the same dosage did not induce any of the cited effects and the $Ca^{2+}$ plasma concentration stayed unchanged at 2.38 mmol/L.

Figure 2:
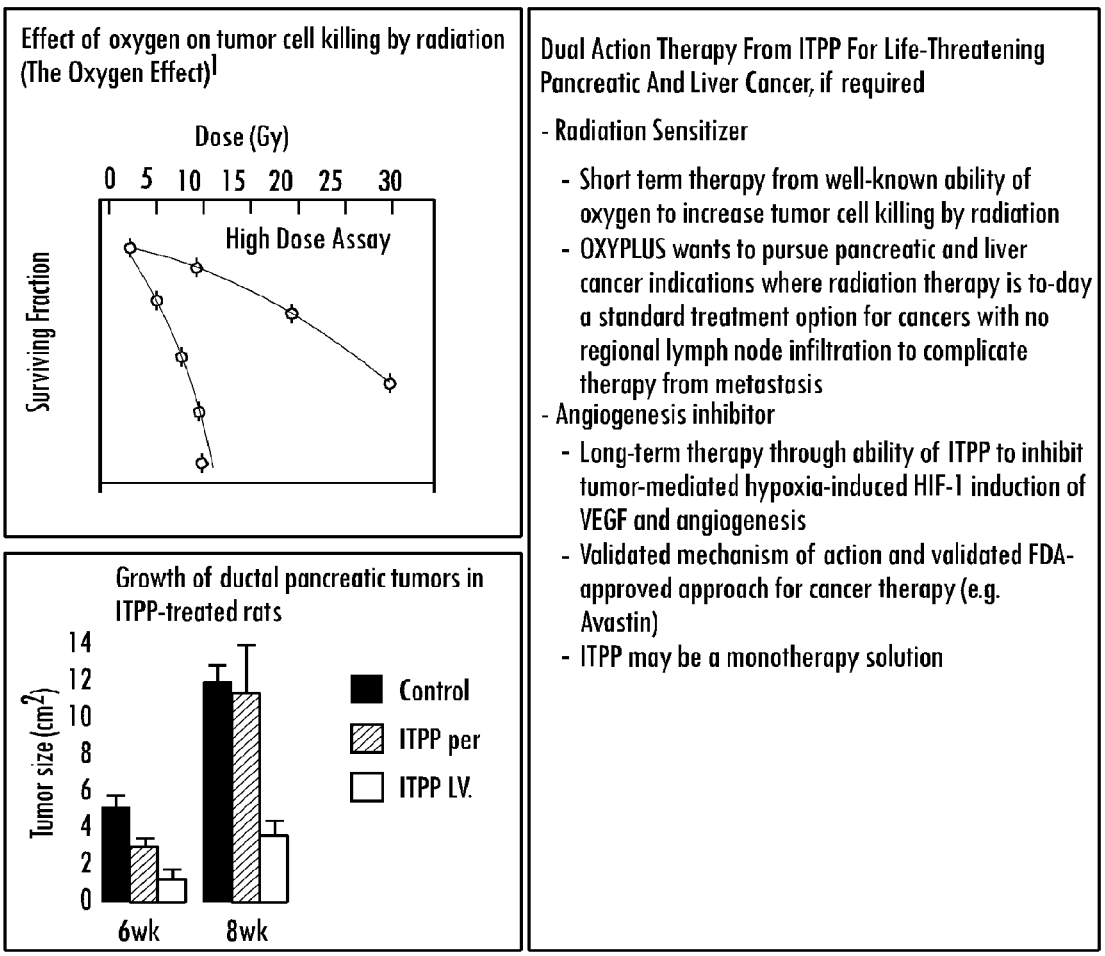
FIG. 2 shows the potential of ITPP-Ca/Na as a dual action radiation sensitizer and angiogenesis inhibitor in pancreatic and rectal cancers.

FIG. 1 shows the ability of ITPP-Ca/Na loaded red blood cells suppression of HIF-1 induction, VEGF and angiogenesis of hypoxic endothelial cells in vitro. FIG. 2 demonstrates the potential of ITPP-Ca/Na as a radiation sensitizer and as an angiogenesis inhibitor in pancreatic and rectal cancers.

TABLE 2

$P_{50}$ values of free Hb after incubation with compounds 4, 5, 7, 11-14 and 15, in vitro

| Compound | $P_{50}$ (Torr) Free Hb | $P_{50}$ (Torr) Hb + compound | $P_{50}$ increase (%) + SD |
|---|---|---|---|
| 4 | (H) 15.3 | 31.6 | 107 ± 22 |
|   | (M) 25.0 | 50.0 | 100 ± 18 |
| 5 | (H) 15.3 | 49.8 | 225 ± 19 |
|   | (M) 24.9 | 69.7 | 180 ± 25 |
|   | (P) 22.0 | 68.1 | 209 ± 39 |
| 7 | (M) 24.9 | 45.1 | 81 ± 15 |
| 11 | (M) 24.9 | 43.8 | 71 ± 3 |
| 12 | (M) 24.9 | 30.6 | 23 ± 5 |
| 13 | (M) 23.4 | 67.7 | 189 ± 43 |
| 14 | (M) 23.4 | 82.9 | 254 ± 49 |
| 15 | (H) 123 | 33.1 | 170 ± 32 |
|   | (M) 26.9 | 61.9 | 130 ± 30 |

H = human; M = murine; P = porcine free Hb. Concentration of the compound solution was 60 mM; means of $P_{50}$ shifts in % are shown. SD = standard deviation. Compounds 4, 7, 11, 12, 14 and 15: three $P_{50}$ values each were used for the calculation of means; compound 5: with human blood: five values, murine blood: ten values and porcine blood; three values were used for the calculation of the means of $P_{50}$ shifts in %.

TABLE 3

$P_{50}$ values of whole blood after incubation with compounds 4, 5, 7, 11-14 and 15, in vitro

| Compound | $P_{50}$ (Torr) whole blood | $P_{50}$ (Torr) compound + whole blood | $P_{50}$ increase (%) + SD |
|---|---|---|---|
| 4 | (H) 22.1 | 24.3 | 10 ± 4 |
|   | (M) 37.9 | 42.7 | 13 ± 2 |
| 5 | (H) 22.1 | 30.8 | 39$^a$ ± 5 |
|   | (P) 31.6 | 44.2 | 40$^a$ ± 3 |
|   | (M) 36.7 | 47.4 | 29$^b$ ± 3 |
| 7 | (M) 40.1 | 52.0 | 30 ± 3 |
| 11 | (M) 37.9 | 45.5 | 20 ± 2 |
| 12 | (M) 37.9 | 41.3 | 9 ± 1 |

TABLE 3-continued $P_{50}$ values of whole blood after incubation with compounds 4, 5, 7, 11-14 and 15, in vitro

| Compound | $P_{50}$ (Torr) whole blood | $P_{50}$ (Torr) compound + whole blood | $P_{50}$ increase (%) + SD |
|---|---|---|---|
| 13 | (M) 37.9 | 41.7 | 10 ± 2 |
| 14 | (M) 39.2 | 41.9 | 7 ± 1 |
| 15 | (M) 39.2 | 42.3 | 8 ± 2 |
|   | (H) 24.8 | 31.0 | 25 ± 3 |
|   | (M) 40.1 | 55.3 | 38$^a$ ± 4 |

H = human; M = murine; P = porcine whole blood. Compound concentrations: 30 mM; means of (four single values) $P_{50}$ shifts □ SD are shown.
$^a$Compound concentration: 60 mM.
$^b$Compound concentration: 4 mM.

Example 2

Effect of in Vivo Lowering of Hemoglobin's Affinity for 09 by ITPP on Intratumoral $PO_2$ Angiogenesis and Expression of VEGF mRNA ITPP, when administered orally, intravenously, or intraperitoneally, inhibits angiogenesis in growing tumors by enhancing the $PO_2$ in the forming tumors. Thirty (30) C57BL/6 mice received 20 g/L of ITPP orally until the $P_{50}$ value showed a shift of at least 20% above the control value. Thereafter, all animals received 1×10$^6$ Lewis Lung carcinoma (LLC) cells, injected in the dorsal cavity. At different time points, the VEGF mRNA were assayed by RT-PCR in the tumors growing in both groups of mice.

Tumor tissue samples were ground in a RIPA lysis buffer (1% Nonidet p-40 detergent, 50 mM Tris pH 8.0, 137 mM NaCl, 10% glycerol) supplemented with protease inhibitor cocktail (Roche, Reinach, Switzerland). After centrifugation for 10 minutes at 4° C. and 12,000 g, protein concentrations of tissue extracts were determined according to the Bradford method. Detergent soluble protein samples (10 mg) were separated by size on a SDS-PAGE in 10% acrylamide gels and transferred to nitrocellulose membrane (Protran BA 85, Schleicher and Schuell, Dassel, Germany). Membranes were blocked for 3 hours at room temperature in 10% skim milk in Tris buffer saline containing 0.1% Tween, before an overnight incubation at 4° C. with rabbit polyclonal antibodies recognizing human, mouse and rat vascular endothelial growth factor (VEGF A-20, sc-152, Santa Cruz Biotechnology, Santa Cruz, Calif.) at a dilution of 1:200. Membranes were then probed for primary antibody with anti-rabbit (1:16,000) peroxidase conjugates (Sigma-Aldrich, L'Isle d'Abeau Chesnes, France) for 60 minutes at room temperature. The resulting complexes were visualized by enhanced chemiluminescence autoradiography (Amersham Pharma Biotech, Orsay, France).

Figure 3:
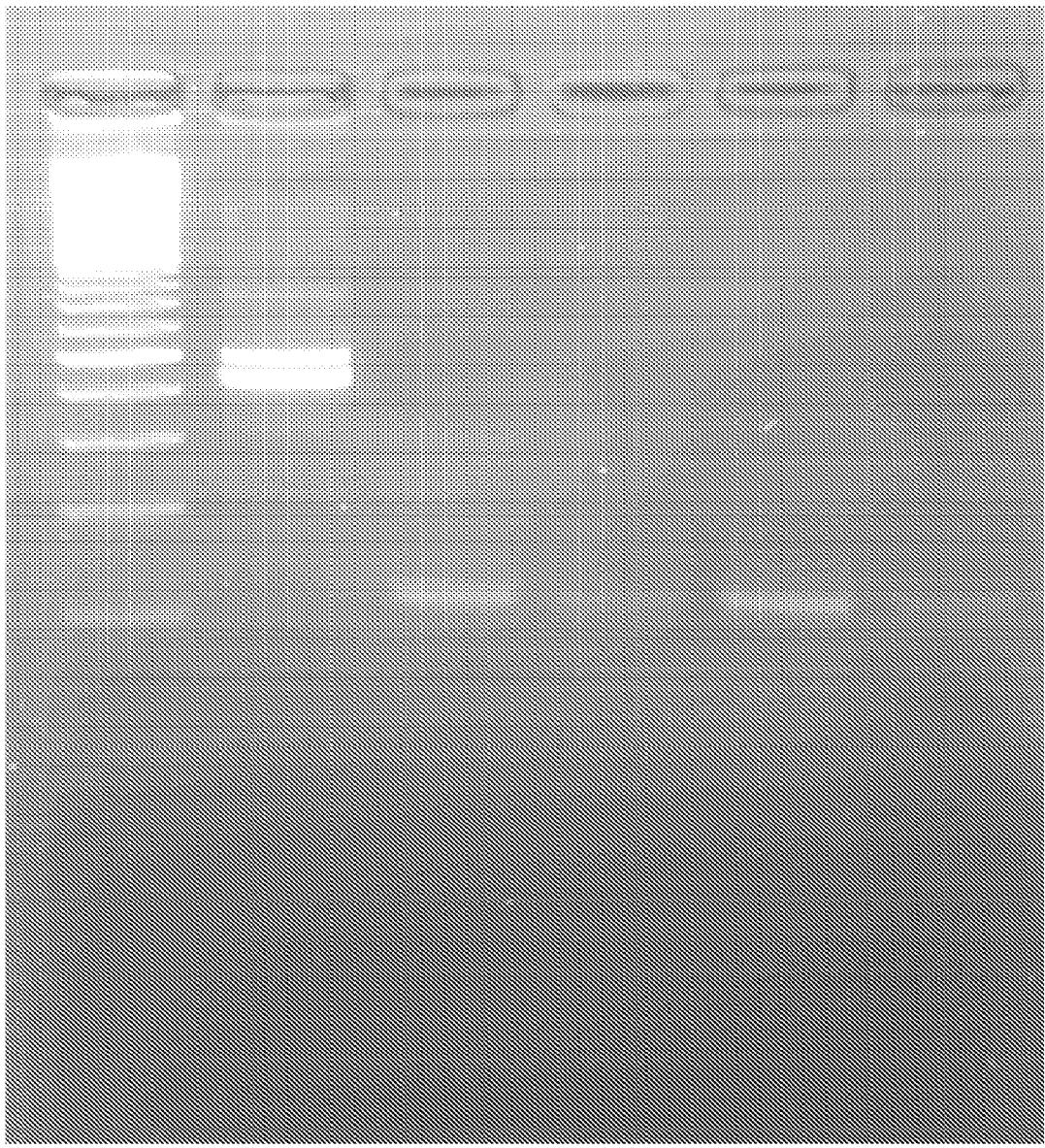
FIG. 3 shows an agarose gel indicating the VEGF mRNA concentrations in tumors from control and ITPP drinking animals.
Figure 4:
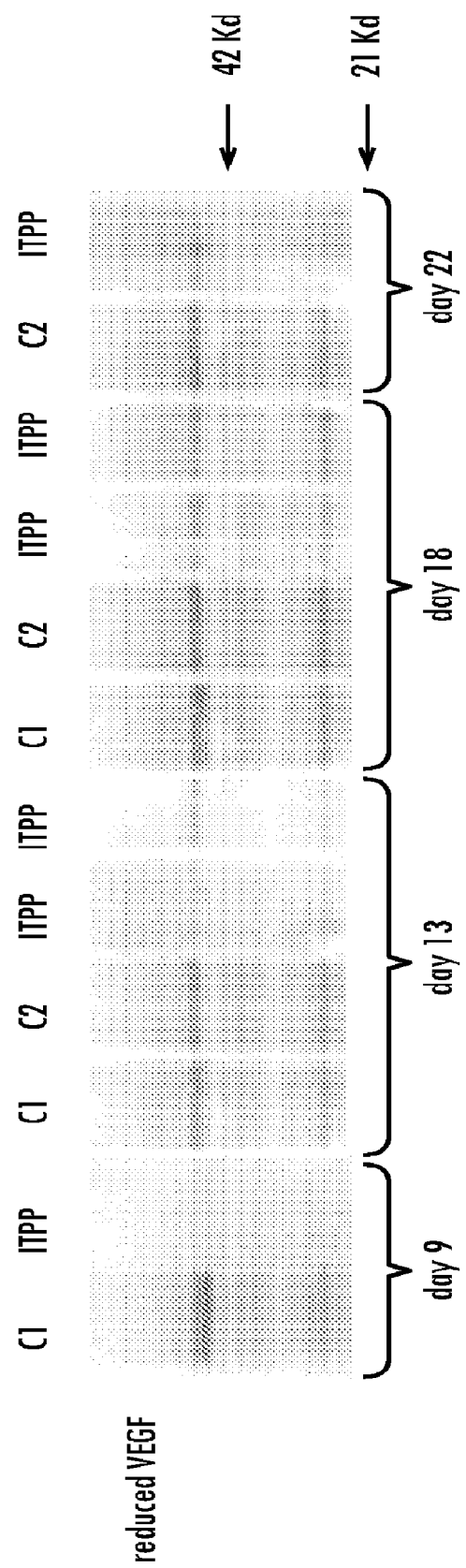
FIG. 4 show a Western blot assay of expressed VEGF in tumors of control and ITPP-treated Lewis Lung carcinoma (LLC) tumor-bearing animals.

There was a difference in the level of mRNA of the VEGF gene in both groups. FIG. 3 shows an agarose gel indicating the VEGF mRNA concentrations in tumors from control and ITPP drinking animals. The RT-PCR agarose gel assay of VEGF mRNAs from tumor tissue taken from 2 mice each on day 15 after inoculation of LLC cells (track 1: controls, track 2: ITPP treated animals) and day 30 after inoculation (track 3: control animals, track 4: ITPP treated animals). FIG. 4 shows the Western blot assay of the expressed VEGF in tumors of control and ITPP-treated LLC tumor-bearing animals.

Quantification of the gel assays indicated a reduction by a factor of 10,000 of the amount of VEGF mRNAs detected in the tumors of animals having received ITPP, at day 9 and then, while differences remain between treated and untreated animals, they tend to decrease. This indicates that ITPP taken up by circulating red blood cells significantly increases tumor $PO_2$.

Example 3

Method of Synthesizing Monocalcium Tetrasodium myo-Inositol Tripyrophosphate

Materials:
1. myo-Inositol hexakisphosphate dodecasodium salt (Product Number: P0109, Sigma).
2. Dicyclohexylcarbodiimide (Product Number: D80002, Aldrich).
3. Triethylamine (Product Number: 15791, Acros)
4. Dowex 50W×8 hydrogen form (Product Number: 217506, Aldrich).
5. $Ca(OH)_2$ (Product Number: 239232, Aldrich).
6. NaOH (Product Number: 1040017, Sds).
7. Acetonitrile (Product Number: 34851, Aldrich).
8. Deionized Water.

Figure 5:
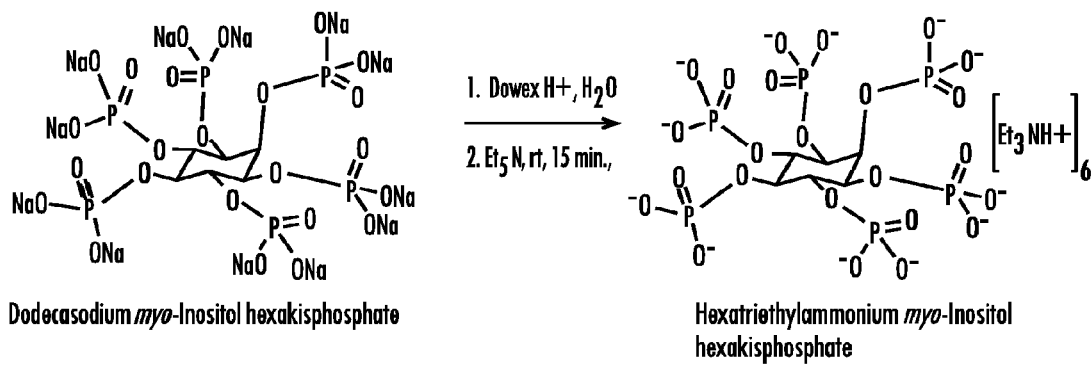
FIG. 5 shows a synthesis scheme for synthesizing the monocalcium tetrasodium salt of myo-inositol 1,6:2,3:4,5 tripyrophosphate.
Figure 5:
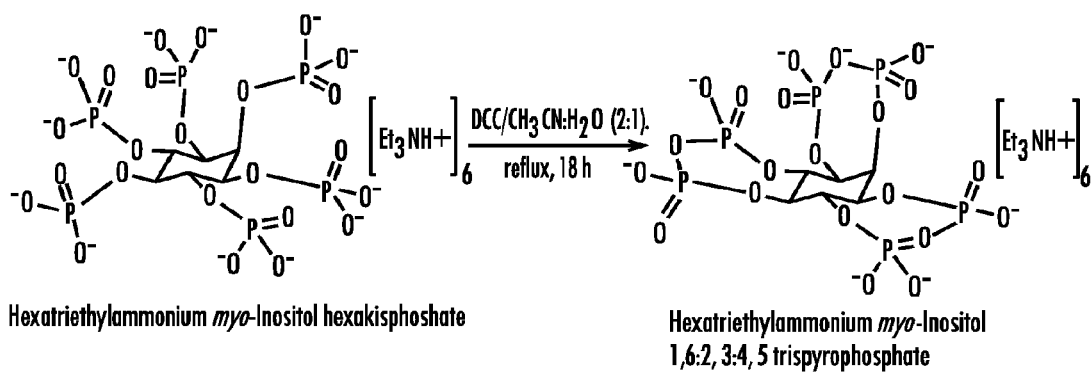
Figure 5:
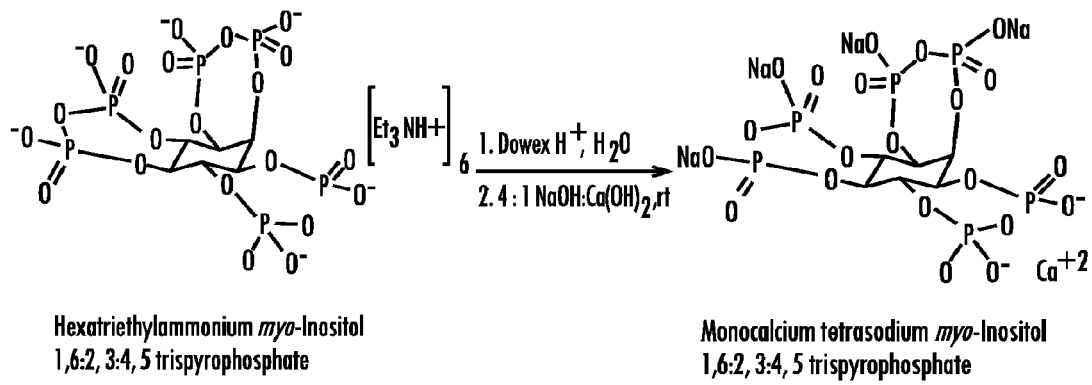

Procedure:

The following synthesis scheme is shown in FIG. 5. Dowex 50WX8-200 ion exchange resin (800 g) was washed with water until the elute was colorless. myo-Inositol hexakisphosphate dodecasodium salt (note-1) (100 g, 0.108 mol, 1.0 eq) was added portionwise (10 g/portion in about 45 minutes) to 500 mL of water. Each portion was dissolved with stirring at room temperature (23° C.) before the next portion was added. This solution was then passed through the column containing the above washed Dowex 50WX8-200 ion exchange resin and eluted with water (4×200 mL) to obtain the free phytic acid (note-2). To the combined acidic fractions, triethylamine (400 mL, 2.87 mol, 26.5 eq, about twice the theoretical quantity) was added over 1 to 2 minutes at room temperature (23° C.) and the mixture was stirred vigorously for 15 minutes (note-3). Then the solvent was evaporated on a rotary evaporator (60° C., 68-22 mbar) (note-4) and the residue was dried under high vacuum for 1 hr at room temperature (23° C.) to give the hexatriethylammonium myo-inositol hexakisphosphate (note-5).

To this hexatriethylammonium myo-inositol hexakisphosphate dissolved in water (800 mL), dicyclohexylcarbodiimide (142 g, 0.68 mol, 6.3 eq) dissolved in acetonitrile (1600 mL) was added at once and the mixture was refluxed for 12 h (note-6). One more equivalent of dicyclohexylcarbodiimide (22 g, 0.108 mol, 1.0 eq) dissolved in acetonitrile (40 mL) was added and refluxed for further 6 h (note-7). The mixture was cooled to room temperature (23° C.) and the dicyclohexylurea formed was filtered through a sintered funnel (note-8) and washed with water (3×200 mL). The filtrate was evaporated on a rotary evaporator (60° C., 68-22 mbar) and dried under high vacuum at room temperature (23° C.) (note-9). The resulting sticky syrupy residue was redissolved in 400 mL of water to remove all dicyclohexylurea that had remained dissolved in acetonitrile, filtered through a sintered funnel (note-8), and washed with water (2×100 mL). The filtrate was evaporated on a rotary evaporator (60° C., 68-22 mbar) and dried under high vacuum at room temperature (23° C.). The resulting residue was redissolved in 200 mL of water to remove any further dicyclohexylurea that had remained dissolved in solution, filtered through a sintered funnel (note-8), and washed with water (2×100 mL). The filtrate was evaporated on a rotary evaporator (60° C., 68-22 mbar) and dried under high vacuum at room temperature (23° C.) affording hexatriethylammonium myo-inositol 1, 6:2,3:4,5 trispyrophosphate (note-10).

This hexatriethylammonium myo-inositol 1, 6:2,3:4,5 trispyrophosphate salt was dissolved in 400 mL of water, passed through a column (note-11) containing prewashed Dowex 50WX8-200 (400 g) ion exchange resin and eluted with water (4×100 mL) (note-12). To the combined acidic fractions was immediately added solid $Ca(OH)_2$ (5.56 g, 0.075 mol, 1.0 eq) followed by addition of a NaOH solution [(12.0 g, 0.300 mol, 4.0 eq) in 25 mL of water)] at room temperature (23° C.) (note-13). Then the pH of the reaction mixture was carefully adjusted to around 6.99 with a solution of 1:4 $Ca(OH)_2$:NaOH (1.5 g of $Ca(OH)_2$ and 3.23 g of NaOH in 1500 mL of water, ~1385 mL brought the pH to ~6.99) (note-14). Finally, the solvent was evaporated on a rotary evaporator (60° C., 68-22 mbar) and dried under high vacuum at room temperature (23° C.) to yield the monocalcium tetrasodium myo-inositol 1,6:2,3:4,5 trispyrophosphate, ITPP Ca4Na (77.2 g, 97%) as a white solid.

The compound obtained has been characterized by proton and phosphorous-31 NMR spectroscopy, mass spectroscopy, elemental analysis, cation determination by atomic absorption and water content. It contains less than 2% other phosphorous compounds. Elemental analysis (ICP atomic absorption): P 20%; Ca 4.2%; Na 10.3% (calc.: P 25.4%; Ca 5.5%; Na 12.6%). Water content: about 18-23% depending on drying conditions.

Notes:
Note-1. Purity checked in-house by $^1H$ and $^{31}P$ NMR (>98%), as well as HPLC, elemental analysis and atomic absorption for cation determination.
Note-2. Collect the elutes which are acidic (pH paper). When all phytic acid is eluted, the elute becomes neutral.
Note-3. Addition of triethylamine generates some heat. Add progressively.
Note-4. Lower temperature can be used if evaporation can be achieved with the equipment available.
Note-5. Purity and characterization was checked by $^1H$ and $^{31}P$ NMR.
Note-6. Reflux temperature was about 80° C. Heated with a mantle.
Note-7. After 12 h, more than 98% product has been formed. Addition of more dicyclohexylcarbodiimide led to >99% product formation.
Note-8. The porosity of the sintered funnel used was 4 and this will effectively filter off the dicyclohexylurea byproduct.
Note-9. Thorough drying is necessary in order to be able to remove all the remaining dicyclohexylurea byproduct.
Note-10. Characterized by $^1H$ and $^{31}P$ NMR, purity >99%.
Note-11. Two typical procedures are for instance:

Procedure 1:

The column frit porosity was 1. The diameter of the column was 8 cm and the length of the Dowex bed was 9.5 cm. The solution was eluted first in 15 minutes without any pressure and then the washings under some pressure were eluted within 5 minutes.

Procedure 2:

The column frit porosity was 2. The diameter of the column was 6 cm and the length of the Dowex bed was 16.5 cm. The solution was eluted first in 45 minutes without any pressure and then the washings under some pressure were eluted within 5-10 minutes.

On the basis of numerous preparations, the following is recommended:

a) a column frit porosity of 1.
b) a Dowex column with a height/diameter ratio of 1.5-2.0, so that the elution time be less than 30 minutes. If the elution is too slow then flush with some pressure.

Note-12. CAUTION: As the myo-inositol 1, 6:2,3:4,5 trispyrophosphate free acid may hydrolyse after standing for a long time at low pH (<1.0), the pH should be adjusted quickly to about 3-4 in order to avoid any such hydrolysis. Check then for absence of triethylamine signals in $^1$H NMR (4-1 ppm) and for absence of phosphorous signals around 2-4 ppm. In the unlikely case that the $^1$H NMR shows the presence of triethylamine, the whole solution has to be passed again over a fresh Dowex-H$^+$ in order to remove it. It is very important that there be no triethylamine left, as it would remain in the final material.

Note-13. It is very important to add first solid $Ca(OH)_2$ and make sure that it is completely dissolved. After addition of the NaOH solution, the pH of the reaction mixture was ~1.6. The total amount of $C(OH)_2$:NaOH required to neutralize the reaction mixture to pH ~6.9 was ~6.9: 14.9 g, respectively. In order to minimize the amount of 1:4 $Ca(OH)_2$:NaOH solution required at the end (and reduce the final volume), add initially 6.3 g of solid $Ca(OH)_2$ followed by 13.6 g of NaOH (in 25 mL of water). Thereafter, the amount of 1:4 $Ca(OH)_2$:NaOH solution required to bring the pH to 6.9-7.0 will be significantly reduced.

Note-14. The 1:4 $Ca(OH)_2$:NaOH solution should be freshly prepared and well closed; otherwise, $CO_2$ from the atmosphere will be absorbed and insoluble materials will be formed. Adjust the pH of the solution close to 7 and do not go beyond 7.

Example 4

Biological Activity of the Monocalcium Tetrasodium Salt of Myo-Inositol Tripyrophosphate (ITPP-Ca4Na)

Figure 6:
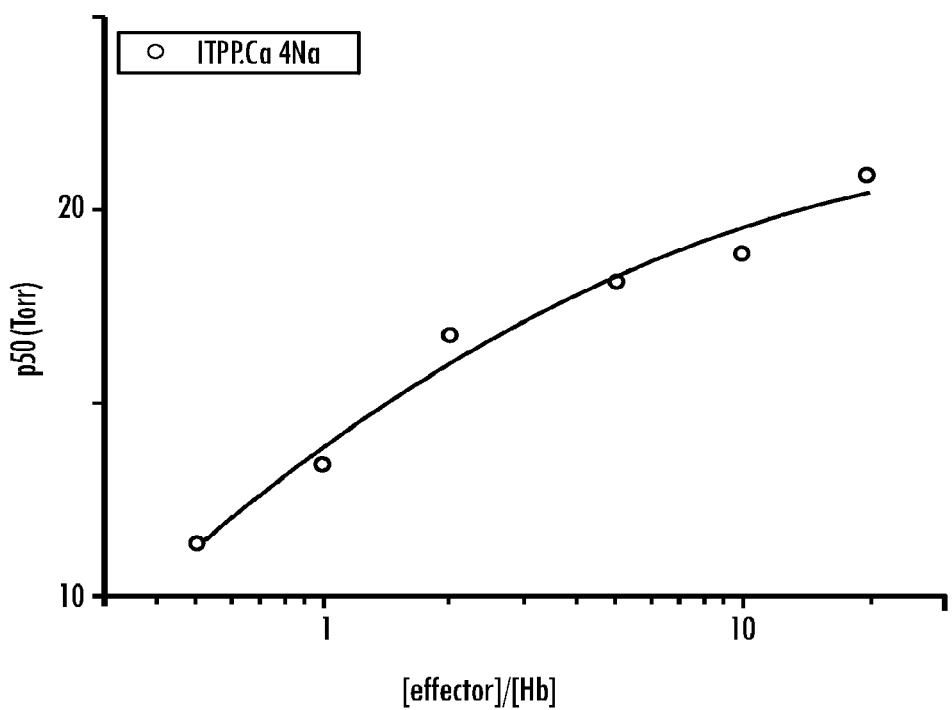
FIG. 6 shows an oxygen fixation curve for hemoglobin after incubation with ITPP-Ca4Na.
Figure 7:
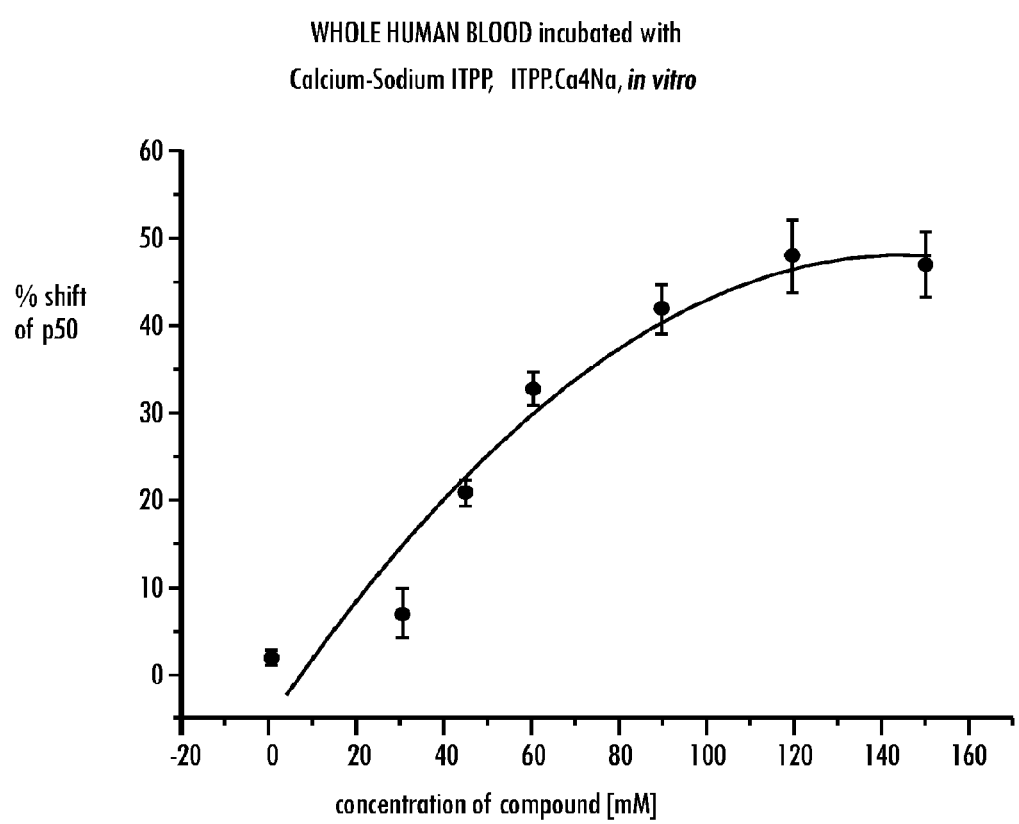
FIG. 7 shows the percent shift of the p50 of whole human blood after incubation with ITPP-Ca4Na.

ITPP-Ca4Na acts as a powerful effector of hemoglobin shifting the oxygen fixation curves to the right, with respect to the natural effector bisphosphoglycerate. The p50 values increase with concentration as show in FIGS. 6 and 7. In FIG. 6, hemoglobin is incubated (at concentrations up to 100 mM final) with ITPP Ca4Na, for 1 hour at 37° C. and measured by TCS-hemox analyzer for p50 shifts. In FIG. 7, whole human blood was incubated (at concentrations up to 120 mM final) with ITPP Ca4Na, for 1 hour 37° C. and measured by TCS-hemox analyzer for p50 shifts.

Having described the invention with reference to particular compositions, method for detection, and source of activity, and proposals of effectiveness, and the like, it will be apparent to those of skill in the art that it is not intended that the invention be limited by such illustrative embodiments or mechanisms, and that modifications can be made without departing from the scope or spirit of the invention, as defined by the appended claims. It is intended that all such obvious modifications and variations be included within the scope of the present invention as defined in the appended claims. It should be understood that any of the above described one or more elements from any embodiment can be combined with any one or more element in any other embodiment. Moreover, when a range is mentioned, it should be understood that it is contemplated that any real number that falls within the range is a contemplated end point. For example, if a range of 0.9 and 1.1 g/kg is given, it is contemplated that any real number value that falls within that range (for example, 0.954 to 1.052 g/kg) is contemplated as a subgenus range of the invention, even if those values are not explicitly mentioned. All references referred to herein are incorporated by reference in their entireties. Finally, the above description is not to be construed to limit the invention but the invention should rather be defined by the below claims.

REFERENCES

1. Fylaktakidou, K., Lehn, J.-M., Greferath, R., and Nicolau, C. (2004) Bioorg. Med. Chem. Lett (submitted)
2. Kim K J, Li B, Winer J, Armanini M, Gillett N, Phillips B E, Ferrara N (1993) Nature 362, 841-844.
3. Kandel J, Bossy-Wetzel E, Radvanyi F, Klagsbrun M, Folkman J, Hanahan D (1991) Cell 66, 1095-1104.
4. O'Reilly M S, Boehm T, Shing Y, Fukai N, Vasios G, Lane W S, Flynn B, Birkhead J R. Olsen B R, Folkman J (1997) Cell 88, 277-285.
5. Good D J, Polyerini P J, Rastinejad F, Le Beau m m, Lemons R S, Frazier W A, Bouck N P. (1990) Proc Natl Acad Sci USA 87, 6624-6628.
6. O'Reilly M S, Holmgren L, Shing Y, Chen C, Rosenthal R. A, Moses M, Lane W S, Cao Y, Sage E H, Folkman J (1994) Cell 79, 315-328.
7. Chen C, Parangi S, Tolentino M J, Folkman J. (1995) Cancer Res. 55, 4230-4233.
8. Ferrara N. (2002) Nat. Rev. Cancer 2, 795-803.
9. Ferrara N, Davis-Smyth T (1997) Endocr Rev. 18, 4-25.
10. Ferrara N, Gerber H P, LeCouter J. (2003) Nat. Med. 9, 669-676.
11. Fontanini G, Vignati S, Boldrini L, Chine S, Silvestri V, Lucchi M, Mussi A, Angeletti C A, Bevilacqua G. (1997) Clin Cancer Res. 3, 861-865.
12. Dory, Porat R, Keshet E. (2001) Am J Physiol Cell Physiol. 280, C1367-1374.
13. Brizel D M, Scully S P, Harrelson J M, Layfield U, Bean J M, Prosnitz L R, Dewhirst M W (1996) Cancer Res. 56, 941-943.

We claim:

1. A method of making a monocalcium tetrasodium salt of myo-inositol 1,6:2,3:4,5 tripyrophosphate comprising;
   a) passing a myo-inositol hexakisphosphate salt over an ion exchange column to obtain a free inositol tripyrophosphate acid,
   b) reacting the free myo-inositol tripyrophosphate acid with triethylamine to form a hexatriethylammonium myo-inositol hexakisphosphate,
   c) reacting the hexatriethylammonium myo-inositol hexakisphosphate with dicyclohexylcarbodiimide dissolved in acetonitrile to form a hexatriethylammonium myo-inositol 1,6:2,3:4,5 trispyrophosphate,
   d) passing the hexatriethylammonium myo-inositol 1,6:2, 3:4,5 trispyrophosphate over an ion-exchange column followed by addition of a calcium salt containing organic compound and a sodium salt containing organic compound to form the monocalcium tetrasodium salt of myo-insotiol 1,6:2,3:4,5 tripyrophosphate.

2. The method of claim 1, wherein the calcium salt containing organic compound is calcium hydroxide and the sodium salt containing organic compound is sodium hydroxide.

* * * * *